(12) United States Patent
Rasoulian et al.

(10) Patent No.: US 10,105,120 B2
(45) Date of Patent: Oct. 23, 2018

(54) METHODS OF, AND APPARATUSES FOR, PRODUCING AUGMENTED IMAGES OF A SPINE

(71) Applicant: The University of British Columbia, Vancouver (CA)

(72) Inventors: Abtin Rasoulian, Vancouver (CA); Robert Rohling, Vancouver (CA); Purang Abolmaesumi, Vancouver (CA); Mehran Pesteie, Vancouver (CA)

(73) Assignee: The University of British Columbia, Vancouver (CA)

( * ) Notice: Subject to any disclaimer, the term of this patent is extended or adjusted under 35 U.S.C. 154(b) by 669 days.

(21) Appl. No.: 14/620,063

(22) Filed: Feb. 11, 2015

(65) Prior Publication Data

US 2015/0223777 A1    Aug. 13, 2015

Related U.S. Application Data

(60) Provisional application No. 61/938,630, filed on Feb. 11, 2014.

(51) Int. Cl.
*A61B 8/00* (2006.01)
*A61B 8/08* (2006.01)
(Continued)

(52) U.S. Cl.
CPC .......... *A61B 8/0875* (2013.01); *A61B 8/0841* (2013.01); *A61B 8/4263* (2013.01);
(Continued)

(58) Field of Classification Search
CPC ..... A61B 8/0841; A61B 8/4263; A61B 8/466; A61B 8/483; A61B 8/4444; A61B 8/4461;
(Continued)

(56) References Cited

U.S. PATENT DOCUMENTS

| | | | | |
|---|---|---|---|---|
| 4,099,250 A | * | 7/1978 | Finnila | G06E 3/001 348/294 |
| 8,509,502 B2 | * | 8/2013 | Porat | G06T 7/11 382/128 |

(Continued)

FOREIGN PATENT DOCUMENTS

| WO | WO 2006/092602 A1 | 9/2006 |
|---|---|---|
| WO | WO 2011/021181 A1 | 2/2011 |

OTHER PUBLICATIONS

Barratt et al., Instantiation and registration of statistical shape models of the femur and pelvis using 3D ultrasound imaging, Medical Image Analysis 12: 358-374, Jan. 29 2008.

(Continued)

*Primary Examiner* — Joel Lamprecht

(74) *Attorney, Agent, or Firm* — Klarquist Sparkman, LLP

(57) ABSTRACT

A computer-implemented method of producing an augmented image of a spine of a patient is disclosed. The method involves: receiving a first ultrasonic volumetric dataset representing a three-dimensional depiction of anatomical features of the spine in a first volume; instantiating a three-dimensional atlas of at least two vertebrae according to the first ultrasonic volumetric dataset; and causing a display to display a rendering of the first ultrasonic volumetric dataset together with a rendering of the atlas. An apparatus for producing the augmented image of the spine of the patient is also disclosed.

24 Claims, 17 Drawing Sheets

(51) Int. Cl.
*G06T 19/00* (2011.01)
*G06T 7/33* (2017.01)

(52) U.S. Cl.
CPC ............ *A61B 8/4444* (2013.01); *A61B 8/466* (2013.01); *A61B 8/483* (2013.01); *G06T 7/33* (2017.01); *G06T 19/00* (2013.01); *A61B 8/4461* (2013.01); *G06T 2200/04* (2013.01); *G06T 2207/10136* (2013.01); *G06T 2207/30012* (2013.01); *G06T 2210/41* (2013.01)

(58) Field of Classification Search
CPC .. G06T 2210/41; G06T 19/00; G06T 2200/04
See application file for complete search history.

(56) References Cited

U.S. PATENT DOCUMENTS

| | | | |
|---|---|---|---|
| 8,666,118 B2 | 3/2014 | Lindholm et al. | |
| 8,696,582 B2* | 4/2014 | Rohling | A61B 8/0841 600/459 |
| 2010/0298705 A1* | 11/2010 | Pelissier | A61B 8/0833 600/443 |
| 2011/0058720 A1* | 3/2011 | Lu | G06T 7/12 382/131 |
| 2015/0209551 A1* | 7/2015 | Burdette | A61L 29/06 600/411 |

OTHER PUBLICATIONS

Brudfors et al., Towards real-time, tracker-less 3D ultrasound guidance for spine anesthesia, International Journal for Computer Assisted Radiology and Surgery 10: 855-865, Apr. 18 2015.

Chen et al., Ultrasound guided spine needle insertion, Proceedings of SPIE 7625: 762538-1-762538-8, Feb. 24 2010.

Fedorov et al., 3D Slicer as an image computing platform for the Quantitative Imaging Network, Magnetic Resonance Imaging 30: 1323-234, 2012.

Fletcher et al., Statistics of shape via principal geodesic analysis on lie groups, IEEE Conference on Computer Vision and Pattern Recognition 1: 95-101, 2003.

Foroughi et al., Ultrasound bone segmentation using dynamic programming, IEEE Ultrasonics Symposium, pp. 2523-2526, 2007.

Hacihaliloglu et al., Statistical shape model to 3D ultrasound registration for spine interventions using enhanced local phase features, Lecture Notes in Computer Science 8150: 361-368, Sep. 2013.

Khallaghi et al., Registration of a statistical shape model of the lumbar spine to 3D ultrasound images, Medical Image Computing and Computer Assisted Intervention, Part II, Lecture Notes in Computer Science 6362: 68-75, 2010.

Khallaghi et al., Biomechanically constrained groupwise statistical shape model to ultrasound registration of the lumbar spine, Informationa Processing in Computer Assisted Inventions, Lecture Notes in Computer Science 6689: 47-54, Jun. 22, 2011.

Lasso et al., Plus: An Open-Source Toolkit for Ultrasound-Guided Intervention Systems, 4th NCIGT and NIH Image Guided Therapy Workshop, 4: 103, 2011.

Moore et al., Image guidance for spinal facet injections using tracked ultrasound, Medical Image Computing and Computer, Part I, LNCS 5761: 516-523, Sep. 2009.

Myronenko et al., Non-rigid point set registration: coherent point drift, Advances in Neural Information Processing Systems 19: 1009-1016, 2006.

Pesteie et al., Automatic recognition of the target plane in 3D ultrasound with EpiGuide, Workshop Abstract, p. 1, Sep. 2014.

Pesteie et al., Real-time ultrasound image classification for spine anesthesia using local directional Hadamard features, International Journal for Computer Assisted Radiology and Surgery 10: 901-912, Apr. 23, 2015.

Rajamani et al., Statistical deformable bone models for robust 3D surface extrapolation from sparse data, Medical Image Analysis, 11: 99-109, 2007.

Rasoulian et al., Probabilistic registration of an unbiased statistical shape model to ultrasound images of the spine, Proceedings of SPIE 8316: 83161P-1-83161P-6, Mar. 5, 2012.

Rasoulian et al., Group-wise registration of point sets for statistical shape models, IEEE Transactions of Medical Imaging, 31: 2025-2034, Jun. 5, 2012.

Rasoulian et al., Lumbar spine segmentation using a statistical multi-vertebrae anatomical shape+pose model, IEEE Transactions on Medical Imaging 32: 1890-1900, Jun. 12, 2013.

Rasoulian et al., Augmentation of paramedian 3D ultrasound images of the spine, International Conference on Information Processing in Computer-Assisted Interventions, Lecture Notes in Computer Science 7915: 51-60, Jun. 26, 2013.

Rasoulian et al., A system for ultrasound-guided spinal injections: a feasibility study, International Conference on Information Processing in Computer-Assisted Interventions, Lecture Notes in Computer Science 8498: 90-99, Jun. 28, 2014.

Rasoulian et al., Ultrasound-guided spinal injections: a feasibility study of a guidance system, International Journal for Computer Assisted Radiology and Surgery 10: 1417-1425, Jun. 3, 2015.

Talib et al., A comparison study assessing the feasibility of ultrasound-initialized deformable bone models, Computer Aided Surgery 10: 293-299, Sep./Nov. 2005.

Tokuda et al., OpenIGTLink: an open network protocol for image-guided therapy environment, International Journal of Medical Robotics 5: 423-434, Dec. 2009.

Winter et al., Registration of CT and Intraoperative 3-D Ultrasound Images of the Spine Using Evolutionary and Gradient-Based Methods, IEEE Transactions on Evolutionary Computation 12: 284-296, Jun. 2008.

* cited by examiner

METHODS OF, AND APPARATUSES FOR, PRODUCING AUGMENTED IMAGES OF A SPINE

CROSS-REFERENCE TO RELATED APPLICATION

This application claims priority to U.S. provisional patent application No. 61/938,630 filed on Feb. 11, 2014. The entire contents of U.S. provisional patent application No. 61/938,630 are incorporated by reference herein.

FIELD

This disclosure relates generally to imaging, and more particularly to methods of, and apparatuses for, producing augmented images of a spine of a patient.

RELATED ART

An epidural needle insertion involves inserting an injection needle in an epidural space in the outermost part of the spinal canal of a patient. The epidural space is the space within the spinal canal (formed by surrounding vertebrae) lying between the dura mater and ligamentum flavum. A facet joint injection involves inserting an injection needle in a facet joint between adjacent vertebrae of a patient. Both epidural needle insertions and facet joint injections are important procedures for spinal anesthesia, but both require careful placement of the injection needle to ensure effective therapy delivery and to avoid damaging the patient's spinal cord.

Conventional procedures to position an injection needle for epidural needle insertions and for facet joint injections either rely solely on a sense of touch, or require costly and potentially harmful X-ray fluoroscopy. Ultrasound sonography can avoid the ionizing radiation that is required for X-ray fluoroscopy, but interpreting ultrasound images is difficult, partly because ultrasound images have limited resolution and partly because ultrasound images can illustrate only limited anatomical features of a spine of a patient. Further, some methods of ultrasound sonography require tracking hardware that tracks positions of a hand-held ultrasound probe, and such tracking hardware can be costly.

SUMMARY

According to one embodiment, there is disclosed a computer-implemented method of producing an augmented image of a spine of a patient, the method comprising: receiving a first ultrasonic volumetric dataset representing a three-dimensional depiction of anatomical features of the spine in a first volume; instantiating a three-dimensional atlas of at least two vertebrae according to the first ultrasonic volumetric dataset; and causing a display to display a rendering of the first ultrasonic volumetric dataset together with a rendering of the atlas.

According to another embodiment, there is disclosed an apparatus for producing an augmented image of a spine of a patient, the apparatus comprising a display and at least one processor circuit in communication with the display. The at least one processor circuit is configured to: receive a first ultrasonic volumetric dataset representing a three-dimensional depiction of anatomical features of the spine in a first volume; instantiate a three-dimensional atlas of at least two vertebrae according to the first ultrasonic volumetric dataset; and cause the display to display a rendering of the first ultrasonic volumetric dataset together with a rendering of the atlas.

Other aspects and features will become apparent to those ordinarily skilled in the art upon review of the following description of illustrative embodiments in conjunction with the accompanying figures.

DETAILED DESCRIPTION

Figure 1:
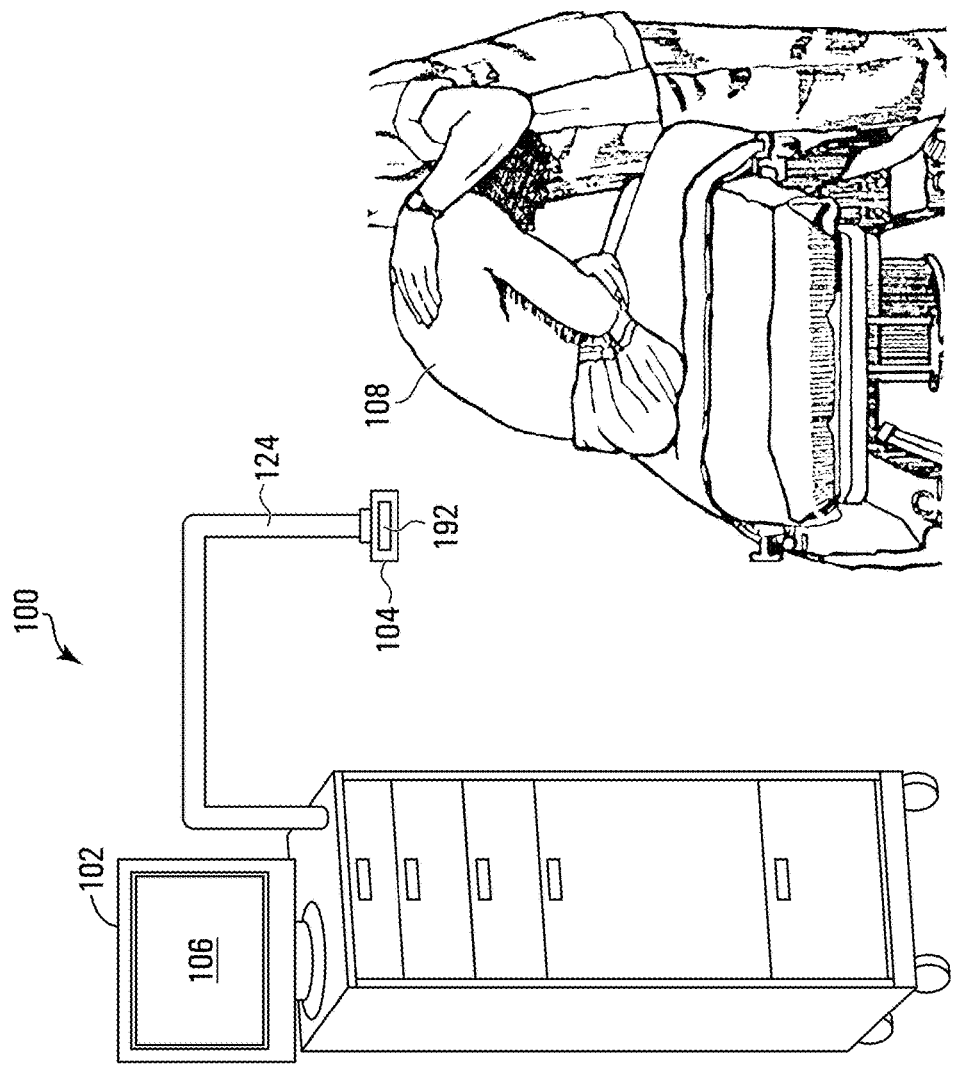
FIG. 1 is an illustration of an image generation system according to one embodiment.

Referring to FIG. 1, an image generation system according to one embodiment is shown generally at 100. The system 100 includes a computer 102 and a hand-holdable ultrasound probe 104 such as an m4DC7-3/4C ultrasound probe from Ultrasonix Medical Corporation in Richmond, British Columbia, Canada. The computer 102 includes a display 106 for displaying images acquired from a patient 108 using the ultrasound probe 104.

Figure 2:
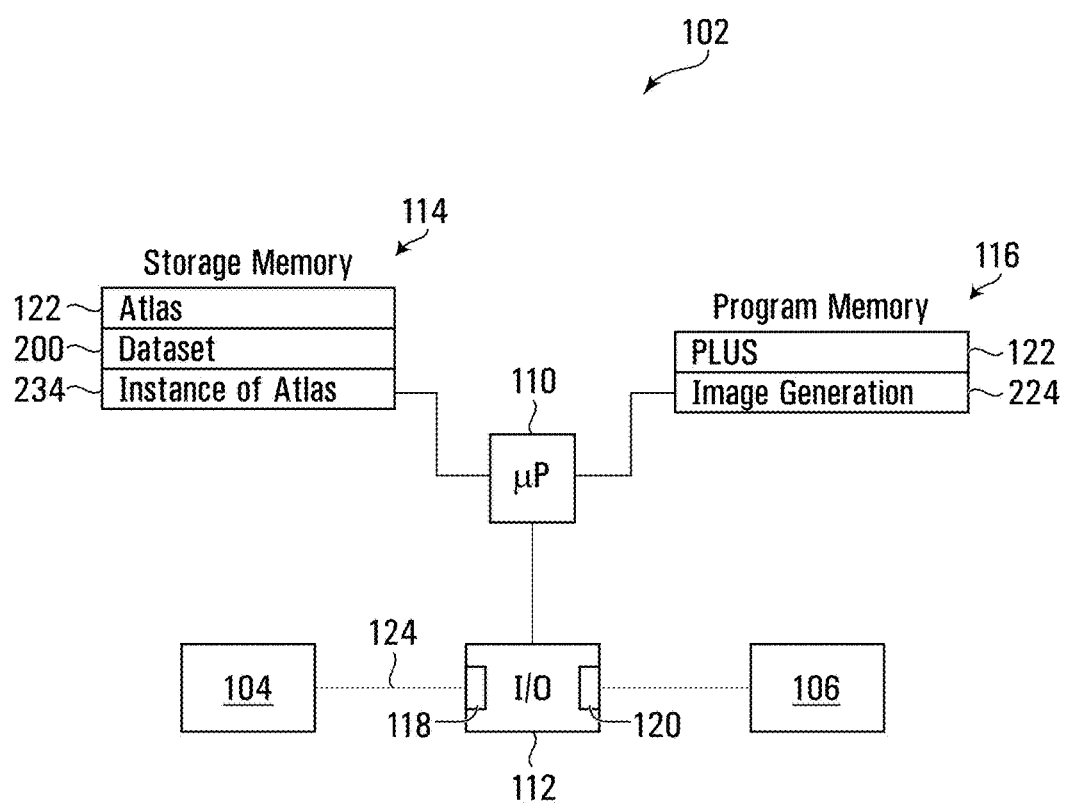
FIG. 2 is a schematic illustration of a processor circuit of the image generation system of FIG. 1.

Referring to FIG. 2, the computer 102 includes a processor circuit including a microprocessor 110, and including an input/output ("I/O") interface 112, a storage memory 114, and a program memory 116 all in communication with the microprocessor 110. The I/O interface 112 includes a signal interface 118 for receiving signals representing input from the ultrasound probe 104, and a signal interface 120 for transmitting signals to the display 106. In general, the storage memory 114 stores data to facilitate various functions of the computer 102, and the program memory 116 stores program codes for directing the microprocessor 110 to implement various functions of the computer 102. The storage memory 114 and the program memory 116 may be implemented on one or more computer-readable and/or computer-writable memory such as one or more of a random-access memory ("RAM") or a hard disc drive ("HDD"), or a combination of one or more RAM and of one or more HDD.

The computer 102 as shown is an example only, and alternative embodiments may include computers that differ from the computer 102. Further, in some embodiments, the functions of the computer 102 as described herein may be separated into separate and different processor circuits. For example, in some embodiments, some of the functions of the computer 102 may be implemented in an ultrasound server computer programmed for some general-purpose functions related to acquiring ultrasound data, and some other functions of the computer 102 may be implemented in a client computer programmed for some client-specific functions as described below. Such a client and server may be connected on an Open Network Interface for Image-Guided Therapy ("OpenIGTLink") network (see http://openigtlink.org/for example).

Atlas

In general, "atlas" may refer to a statistical model of anatomical features. In the embodiment shown in FIG. 2, the storage memory 114 includes an atlas store 122 that stores computer-readable codes representing an atlas of at least two adjacent human lumbar vertebrae, although atlases in alternative embodiments may represent other vertebrae (such as cervical, thoracic, or sacral vertebrae, or a combination of two or more thereof) or still other anatomical features.

Statistical Shape Model

The atlas in some embodiments is a statistical shape model, and in such embodiments, the computer-readable codes in the atlas store 122 represent a mean shape and modes of variation of the mean shape identified from training data acquired from a training population sample using computed tomography ("CT") datasets representing measurements of exterior surfaces of at least two vertebrae of the spines from the training population sample of K human spines. Measurements of the kth spine in the training population are represented by $N_k$ points $t_n^k$ in a set of points $T_k$, each point $t_n^k$ representing a measurement of an exterior surface of one of the at least two vertebrae of the kth spine in D spatial dimensions. The mean shape Z of the at least two vertebrae is represented by M points $z_m$ in D spatial dimensions, and M is not necessarily the same as any $N_k$.

A probability density estimation may estimate the mean shape Z and a transformation $\Phi_k$ for each of the K sets of training points, such that the mean shape Z represents a Gaussian Mixture Model ("GMM") centroid, and each training point set represents a data point generated by the model, by minimizing a negative log-likelihood function $$E(\Phi_k, Z) = -\sum_{k=1}^{K}\sum_{n=1}^{N_k}\log\sum_{m=1}^{M}P(m)p(t_n^k \mid \Phi_k(z_m)) \quad \text{(Eq. 1)}$$

using an expectation-maximization algorithm, which is an iterative method that alternates between an expectation step and a maximization step. The expectation step computes a probability of how likely a point in the mean shape generates another point in a training point set according to $$P(z_m \mid t_n^k) = \frac{\exp\left(-\frac{1}{2}\left\|\frac{t_n^k - \Phi_k(z_m)}{\sigma}\right\|^2\right)}{\sum_{j=1}^{N_k}\exp\left(-\frac{1}{2}\left\|\frac{t_j^k - \Phi_k(z_m)}{\sigma}\right\|^2\right)} \quad \text{(Eq. 2)}$$

where $\sigma$ controls uncertainty. Initially, $\sigma$ is chosen to be large, and its value decreases in each iteration. Parameters are updated in the Maximization step to minimize the objective function $$(Z^*, \Phi_z^*) = \underset{Z^*, \Phi_z^*}{\operatorname{argmin}}\sum_{k=1}^{K}\frac{1}{2\sigma_k^2}\sum_{m,n=1}^{M,N_k}P(m \mid t_n^k)\|t_n^k - \Phi_k(z_m)\|^2 + \frac{\lambda}{2}\|L\Phi_k\|^2. \quad \text{(Eq. 3)}$$

The latter term of Eq. 3 is a regularization over the transformations. The objective function can be minimized alternatively with respect to the mean shape and the transformation parameters. For a fixed mean shape, the problem becomes a registration problem and each term of Eq. 3 can be minimized separately. For a given $T_k$ and Z, this minimization is a registration problem as stated and solved in Myronenko, A., Song, X., and Carreira-Perpinan, M., "Non-rigid point set registration: Coherent point drift," *Advances in Neural Information Processing Systems* 19, 1009-1016 (2007), which modeled the deformations and solved the registration step in a closed-form solution using a coherent point drift ("CPD"). For fixed transformations, each point ⊙ of the mean shape can be found separately by minimizing a cost function $$\sum_{k=1}^{K}\sum_{n=1}^{N_k}P(m \mid t_n^k)\|t_n^k - \Phi_k(z_m)\|^2 \quad \text{(Eq. 4)}$$

by finding $z_m$ using a Broyden-Fletcher-Goldfarb-Shanno ("BFGS") quasi-Newton method with a cubic-line search.

The mean shape Z and transformations $\Phi_k$ identified as described above are unbiased because they are not generated according to a "template" spine that may bias the mean shape and transformations. Further, the mean shape Z and transformations $\Phi_k$ identified as described above are part of a single statistical shape model that represents two or more vertebrae, which may account for similar variations in different vertebrae. In other words, when compared to statistical shape models of individual vertebrae, the mean shape Z and transformations $\Phi_k$ identified as described above may more accurately predict variations in a particular spine by predicting variations in one vertebra based on measurements in one or more different vertebra in the same spine.

From the transformations $\Phi_k$ and the mean shape Z, principal component analysis ("PCA") identifies eigenvalues $\lambda_i$ and eigenvectors $v_i$. Each eigenvector $v_i$ represents a respective mode of variation of the mean shape Z. Each eigenvector $v_i$ is associated with a respective eigenvalue $\lambda_i$, which represents the amount of variation that the respective mode of variation accounts for. Representations of the eigenvalues $\lambda_i$, the eigenvectors $v_i$, and the mean shape Z are stored in the atlas store 122 shown in FIG. 2.

Statistical Shape-and-Pose Model

In other embodiments, the atlas is a statistical shape-and-pose model, and in such embodiments, the computer-readable codes in the atlas store 122 represent a mean shape, modes of variation of the mean shape, a mean pose, and modes of variation of the mean shape, also identified from a training population sample using CT datasets representing measurements of exterior surfaces of the spines from the training population.

In the embodiments described herein, statistical shape-and-pose models are generated with pose statistics separated from shape statistics because pose and shape are not necessarily correlated. Further, shape deformations are assumed to lie on a Euclidean space, whereas poses are represented by similarity transformations that form a Lie group, which is a Riemannian manifold in which analysis in Euclidean space is not applicable. A Lie group G is a differentiable manifold where multiplication and inversion are smooth. The tangent space at the identity element is Lie algebra g. The exponential $$\text{mapping } g: \exp(x) \to G,$$

and its inverse logarithm $$\text{mapping } G: \log(x) \to g,$$

are used to map elements in the tangent space into G and vice versa.

Principal geodesics for Lie groups are analogous to principal components in Euclidean space. According to an approximation suggested by Fletcher, P., Lu, C., Joshi, S., "Statistics of shape via principal geodesic analysis on lie groups," *IEEE CVPR* 1, pp. 95-101 (2003), for a set of N elements $x_1, \ldots, x_N$, the mean $\mu$ is found using an iterative approach. Then, PCA is applied to the residuals $\log(\mu^{-1}x_i)$ in the Lie algebra. The results are orthonormal modes of variation v, which give principal geodesics by exponential mapping $\mu \exp(v)$.

As with the statistical shape models described above, the training population sample includes measurements of exterior surfaces of N human spines. Pose statistics represent poses or relative positions of L vertebrae in each of the N human spines. Initially, a group-wise Gaussian mixture model ("GMM")-based registration technique (described in Rasoulian, A., Rohling, R., Abolmaesumi, P., "Group-wise registration of point sets for statistical shape models," *IEEE TMI* 31(11), 2025-2034 (2012)) is used to establish dense correspondences across the training set. Generalized Procrustes analysis is then used to generate a mean pose $\mu_l^p$ and a mean shape $\mu_l^s$ for each the L vertebrae, and to generate transformations $T_{n,l}$. The transformation $T_{n,l}$ is a similarity transformation of the mean pose $\mu_l^p$ and mean shape $\mu_l^s$ of the lth vertebra to the lth vertebra of the nth spine.

The transformations $T_{n,l}$ for all anatomies are concatenated, and then K principal geodesics for pose $\mu_l^p \exp(v_{k,l}^p)$ and K principal geodesics $\mu_l^s \exp(v_{k,l}^s)$ for shape are extracted, where $v_{k,l}^p$ are eigenvectors representing the K principal geodesics for pose of the lth vertebra, and $v_{k,l}^s$ are eigenvectors representing the K principal geodesics for shape of the lth vertebra. Each eigenvector $v_{k,l}^p$ and $v_{k,l}^s$ is associated with a respective eigenvalue $\lambda_{k,l}^p$ or $\lambda_{k,l}^s$, which represents the amount of variation that the respective principal geodesic accounts for. Representations of the eigenvalues $\lambda_{k,l}^p$ and $\lambda_{k,l}^s$, of the eigenvectors $v_{k,l}^p$ and $v_{k,l}^s$, of the mean pose $\mu_l^p$, and of the mean shape $\mu_l^s$ are stored in the atlas store 122 shown in FIG. 2.

Ultrasound Probe

Figure 3:
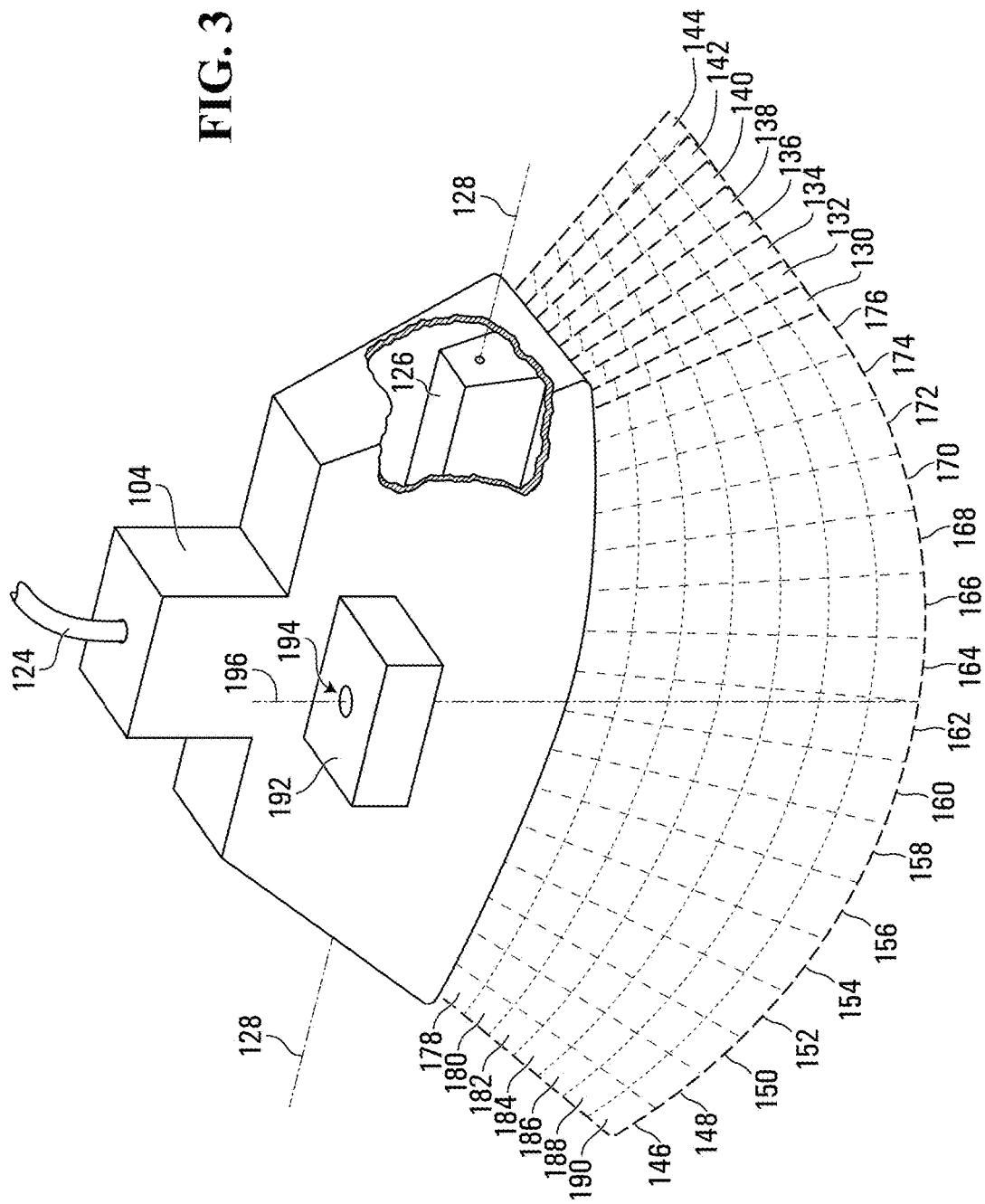
FIG. 3 is a top perspective view of an ultrasound probe of the image generation system of FIG. 1.
Figure 4:
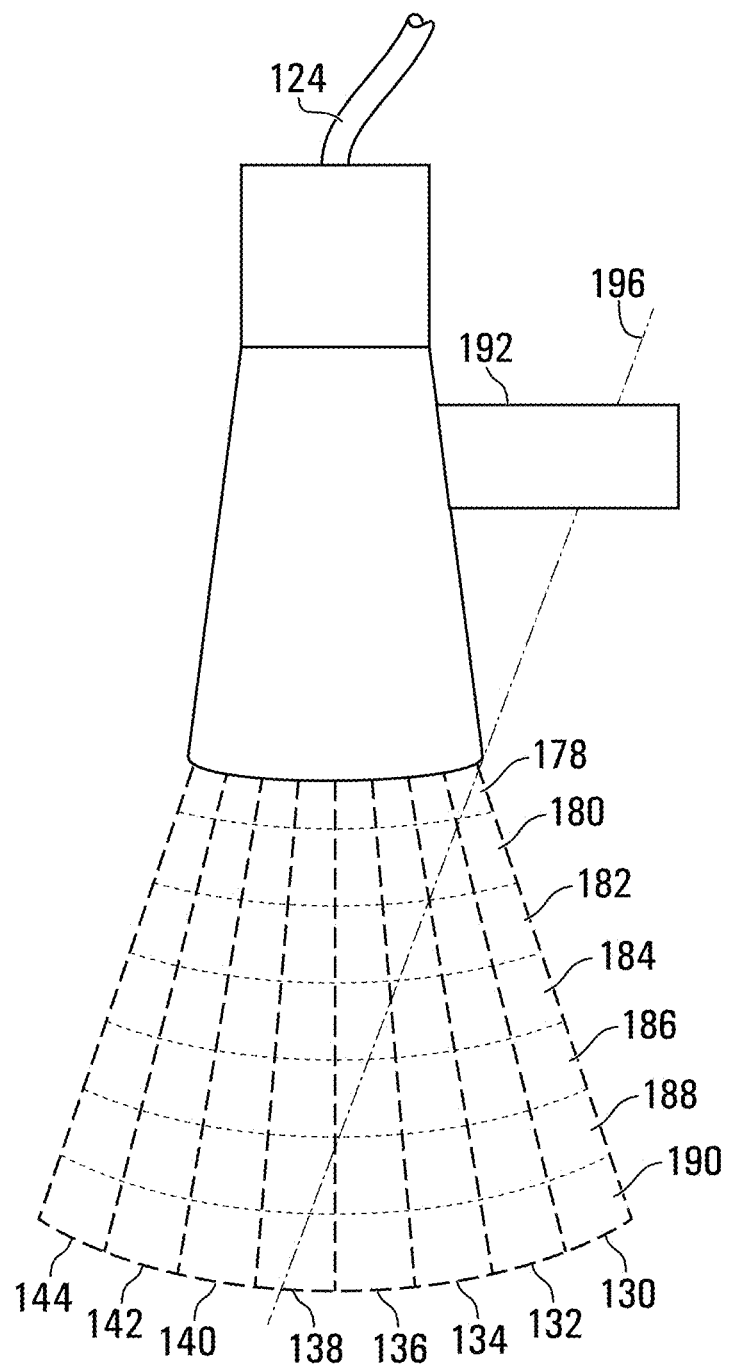
FIG. 4 is an end view of the ultrasound probe of FIG. 3.

Referring to FIGS. 3 and 4, the ultrasound probe 104 includes an ultrasound probe cable 124 in communication with the signal interface 118 (shown in FIG. 2) and a motor-driven ultrasound transducer array 126 inside the ultrasound probe 104. The ultrasound transducer array 126 is rotatable about a longitudinal axis 128 of the ultrasound probe 104. As a motor (not shown) rotates the ultrasound transducer array 126 about the longitudinal axis 128, the ultrasound transducer array 126 moves into various positions. In each such position, the ultrasound transducer array 126 can transmit ultrasound waves into one of various scanning planes and measure reflections of the ultrasound waves from the scanning plane. For simplicity, eight illustrative scanning planes 130, 132, 134, 136, 138, 140, 142, and 144 are shown in FIGS. 3 and 4, although practical embodiments may include many more than eight scanning planes.

When the ultrasound transducer array 126 is positioned to transmit ultrasound waves into one of the scanning planes, the ultrasound transducer array 126 transmits ultrasound waves into various scanning lines in the scanning plane. For simplicity, 16 illustrative scanning lines 146, 148, 150, 152, 154, 156, 158, 160, 162, 164, 166, 168, 170, 172, 174, and 176 in the scanning plane 130 are shown in FIG. 3, although practical embodiments may include many more than 16 scanning lines in each scanning plane.

After transmitting the ultrasound waves into one of the scanning lines in one of the scanning planes, the ultrasound transducer array 126 measures a time series of intensity of reflections of the ultrasound waves. Reflections that are measured relatively soon represent reflections that are closer to the ultrasound transducer array 126, and reflections that are measured relatively late represent reflections that are farther from the ultrasound transducer array 126. Therefore, in each scanning line, a time series of intensity values is measured and represents reflections from various regions in the scanning line, and the intensity measured during a particular interval of time represents intensity of reflections in a corresponding region in the scanning line. For simplicity, seven measurement regions 178, 180, 182, 184, 186, 188, and 190 in the scanning line 146 are shown in FIGS. 3 and 4, although practical embodiments may include many more than seven measurement regions in a scanning line. Reflections that are measured relatively soon represent reflections from the measurement region 178, and reflections that are measured relatively late represent reflections from the measurement region 190.

In each scanning plane (such as the illustrative scanning planes 130, 132, 134, 136, 138, 140, 142, and 144 shown in FIGS. 3 and 4), the ultrasound transducer array 126 measures a time series of intensity of reflections of ultrasound waves in various scanning lines, so each scanning plane represents measurements in two dimensions (one dimension resulting from the different positions of the different scanning lines in the scanning plane, and one dimension from resulting from different distances from the ultrasound transducer array 126 along the scanning lines). To acquire an ultrasonic volumetric dataset, the ultrasound transducer array 126 oscillates between positions to transmit ultrasound waves into each of the scanning planes. The ultrasonic volumetric dataset represents measurements in three dimensions because each of the scanning planes represents measurements in two dimensions, and a third dimension results from the different positions of the different scanning planes. Therefore, intensities measured in all of the measurement regions in the scanning lines represent reflections in the entire three-dimensional volume defined by all of the measurement regions, and the ultrasound probe 104 is accordingly a three-dimensional ultrasound probe.

In some embodiments, the ultrasound probe 104 must be held steady while the ultrasound transducer array 126 measures intensities of reflections of ultrasound waves in the various scanning planes. However, in other embodiments, the ultrasound probe 104 may be moved along the patient's skin (not shown).

The ultrasound probe 104 may include a needle guide 192, which defines a generally cylindrical through-opening shown generally at 194 to receive a portion of an injection needle (not shown). The generally cylindrical through-opening shown generally at 194 guides the injection needle along a generally linear needle trajectory 196, which passes through the volume defined by the measurement regions as shown in FIGS. 3 and 4. In an alternative embodiment, the needle guide 192 may define an open channel, allowing ease of assembly and disassembly, to guide the injection needle along the generally linear needle trajectory 196.

Ultrasonic Volumetric Datasets

Referring back to FIG. 2, an ultrasonic volumetric dataset acquired using the ultrasound probe 104 may be transmitted as one or more signals over the ultrasound probe cable 124 to the signal interface 118. As the signal interface 118 receives the one or more signals over the ultrasound probe cable 124, the microprocessor 110 executes program codes according to the open-source Public Software Library for Ultrasound Imaging Research ("PLUS") library (see https://www.assembla.com/spaces/plus/wiki for example), in PLUS codes 198 in the program memory 116, to generate codes representing an ultrasonic volumetric dataset. For example, the PLUS codes may account for missing frames during the acquisition by applying a hole-filling algorithm to interpolate missing voxels from a Gaussian-weighted average of the cubic neighborhood with a diameter of three voxels and a standard deviation of the Gaussian of 0:667. The PLUS codes may also combine more than one ultrasonic volumetric dataset, such as a plurality of ultrasonic volumetric datasets taken from different angles, by three-dimensional stitching or mosaicing for example, to generate potentially more accurate data. The microprocessor 110 then stores the codes representing the ultrasonic volumetric dataset in an ultrasonic volumetric dataset store 200 in the storage memory 114. The ultrasonic volumetric dataset in the ultrasonic volumetric dataset store 200 may be a representation of pixels or voxels in three-dimensional space. Alternative embodiments may include one or more of various alternatives to PLUS codes.

Figure 5:
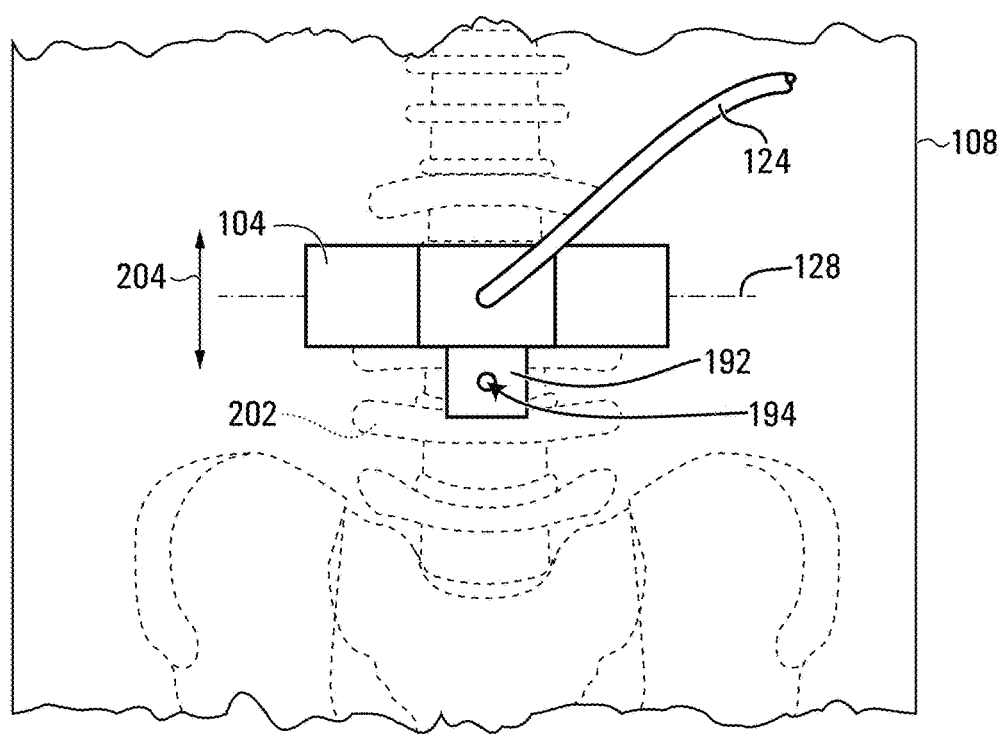
FIG. 5 is an illustration of the ultrasound probe of FIG. 3 over lumbar vertebrae of a patient.

Referring to FIG. 5, a user may position the ultrasound probe 104 on a back of the patient 108 to acquire ultrasonic volumetric datasets of lumbar vertebrae 202 of the patient 108. In many embodiments, the patient 108 was not a member of the training population sample used to generate the atlas. In the embodiment shown in FIG. 5, the longitudinal axis 128 of the ultrasound probe 104 extends laterally across the back of the patient 108, and the user may move the ultrasound probe 104 in a superior-inferior direction 204 to acquire sequential ultrasonic volumetric datasets. The user may also position and hold steady the ultrasound probe 104 on a back of the patient 108 while an injection needle is inserted.

Alternative Ultrasound Probes

Alternative embodiments may acquire an ultrasonic volumetric dataset with ultrasound probes that differ from the ultrasound probe 104. For example, although the ultrasound probe 104 includes a motor-driven ultrasound transducer array 126 to acquire ultrasonic volumetric measurements in three dimensions, alternative three-dimensional ultrasound probes may include matrix-array transducers or double motor-driven transducer arrays for example.

Figure 6:
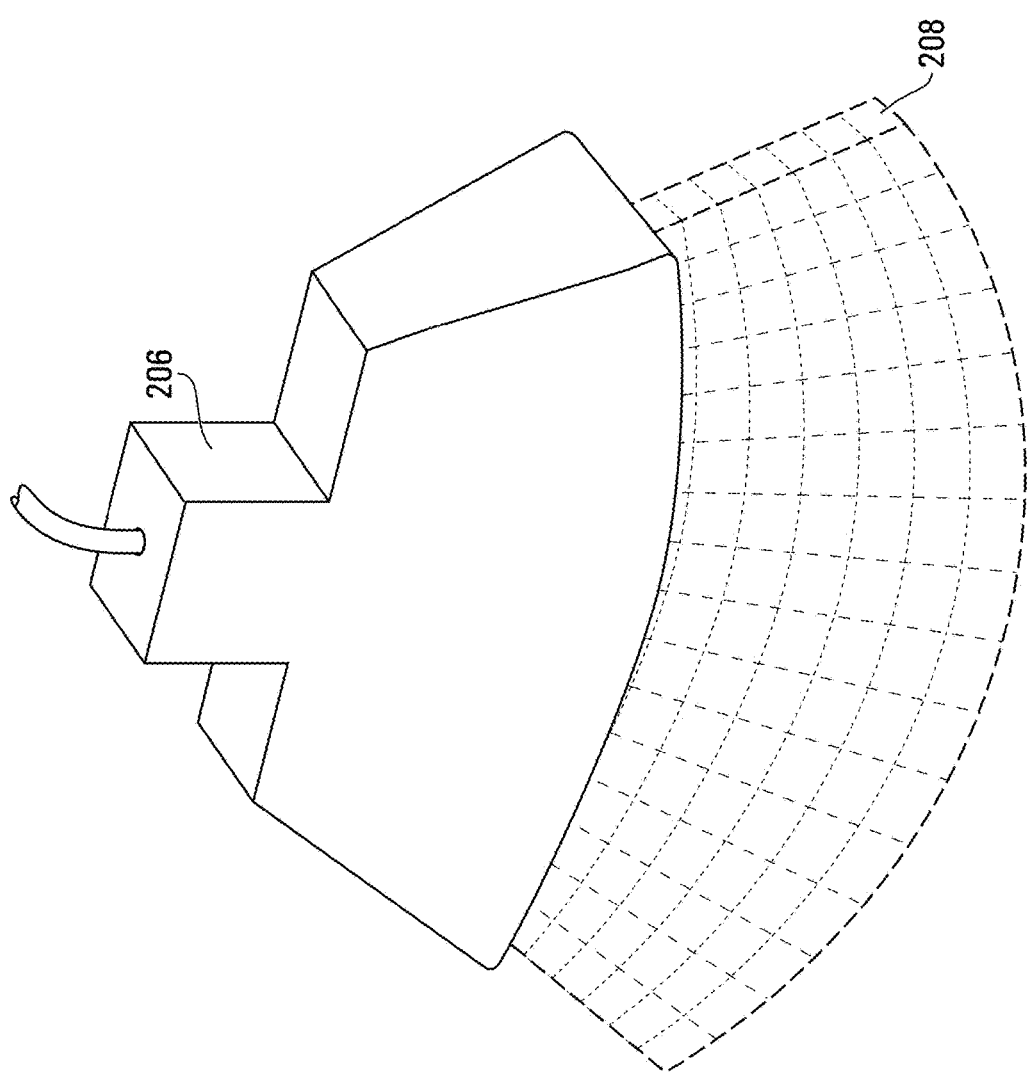
FIG. 6 is a top perspective view of an ultrasound probe of another embodiment.

Also, referring to FIG. 6, a hand-holdable ultrasound probe 206 according to an alternative embodiment includes a fixed or rigidly attached ultrasound transducer array (not shown) inside the ultrasound probe 206. The ultrasound transducer array of the ultrasound probe 206 can transmit ultrasound waves into various scanning lines in a single scanning plane 208 and measure reflections of the ultrasound waves from the scanning plane 208. For simplicity, 16 illustrative scanning lines are shown in the scanning plane 208, although practical embodiments may include many more than 16 scanning lines. As indicated above, a single scanning plane represents measurements in two dimensions, so the ultrasound probe 206 is a two-dimensional ultrasound probe.

Figure 7:
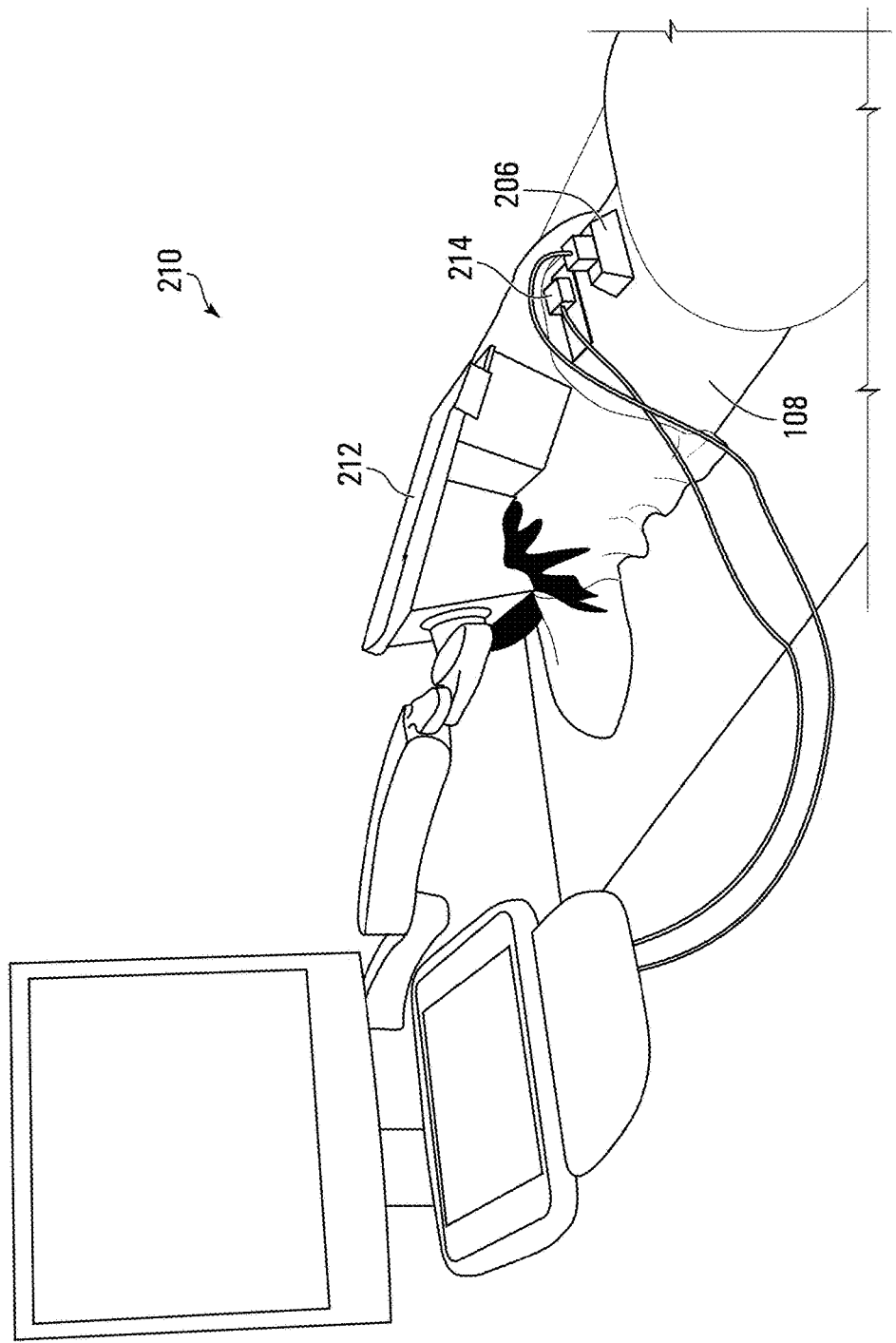
FIG. 7 is an illustration of an image generation system including the ultrasound probe of FIG. 6.

Referring to FIG. 7, an ultrasound system shown generally at 210 includes the ultrasound probe 206, an electromagnetic tracker 212 (such as an Ascension DriveBAY™ tracker from Northern Digital Inc., Waterloo, Ontario, Canada), a tracking reference 214, and an ultrasound computer 216 in communication with the ultrasound probe 206, the tracker 212, and the tracking reference 214. The tracker 212 records a position of the ultrasound probe 206 for each two-dimensional ultrasonic dataset that the ultrasound probe 206 acquires. Further, the tracker 212 records a position of the tracking reference 214 on the patient 108 to account for any movement of the patient 108 during scanning. Therefore, by measuring changes in the position of the ultrasound probe 206 relative to the tracking reference 214, the tracker 212 measures positions of two-dimensional ultrasonic datasets that the ultrasound probe 206 acquires relative to each other and relative to the patient.

Figure 8:
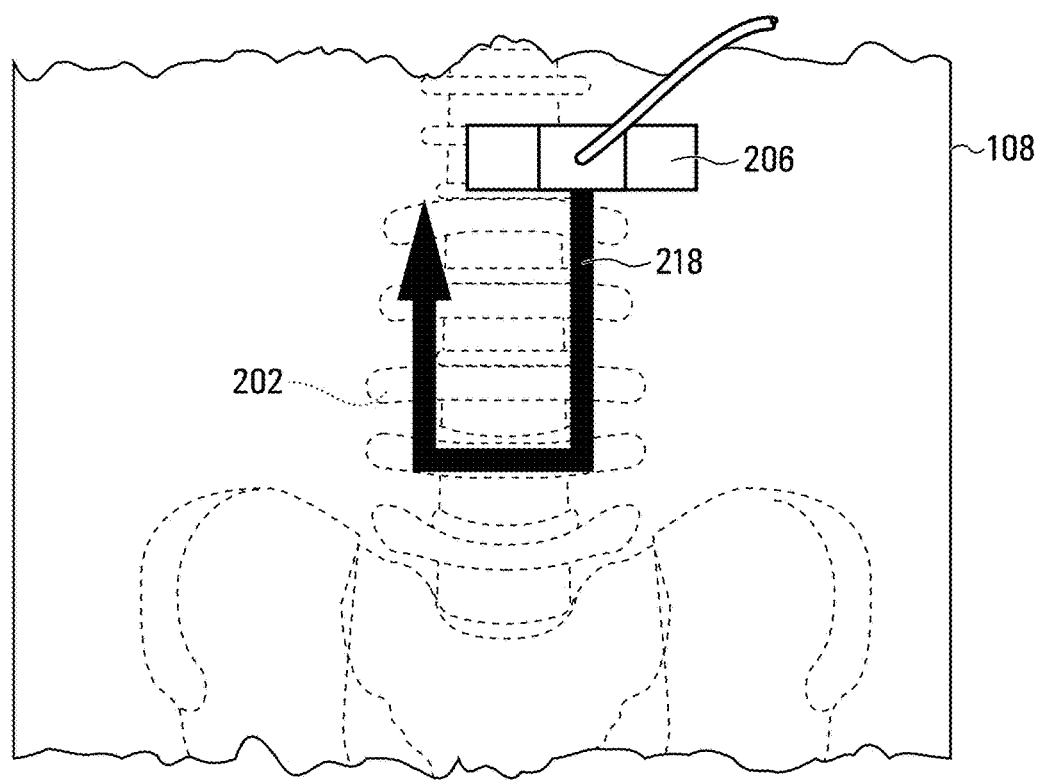
FIG. 8 is an illustration of the ultrasound probe of FIG. 6 over lumbar vertebrae of a patient.
Figure 9:
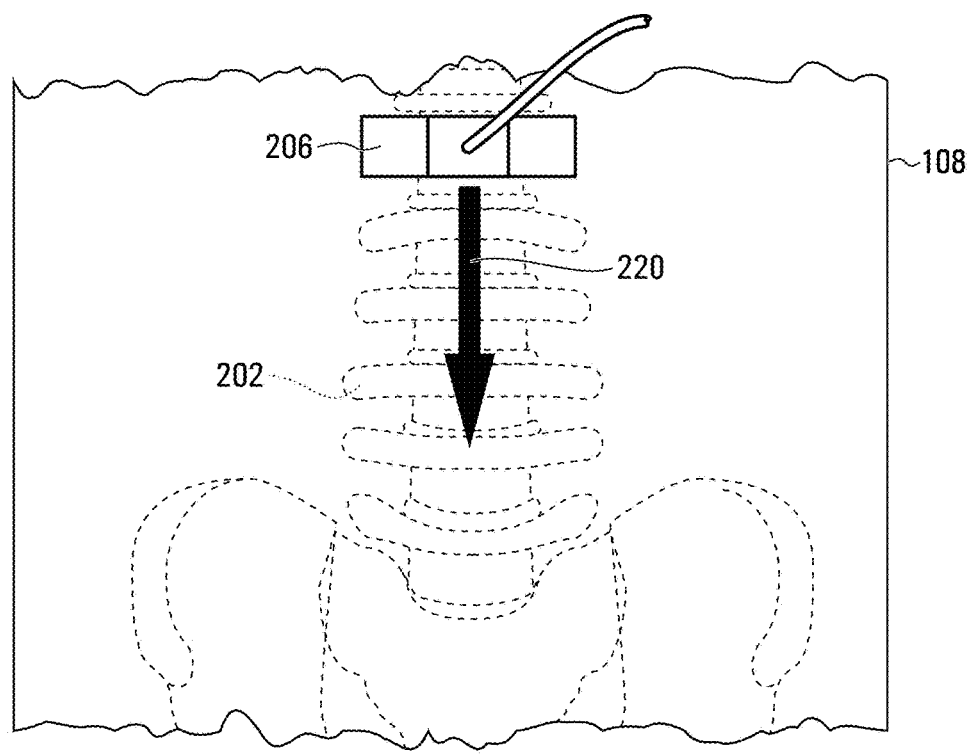
FIG. 9 is another illustration of the ultrasound probe of FIG. 6 over the lumbar vertebrae of the patient.
Figure 10:
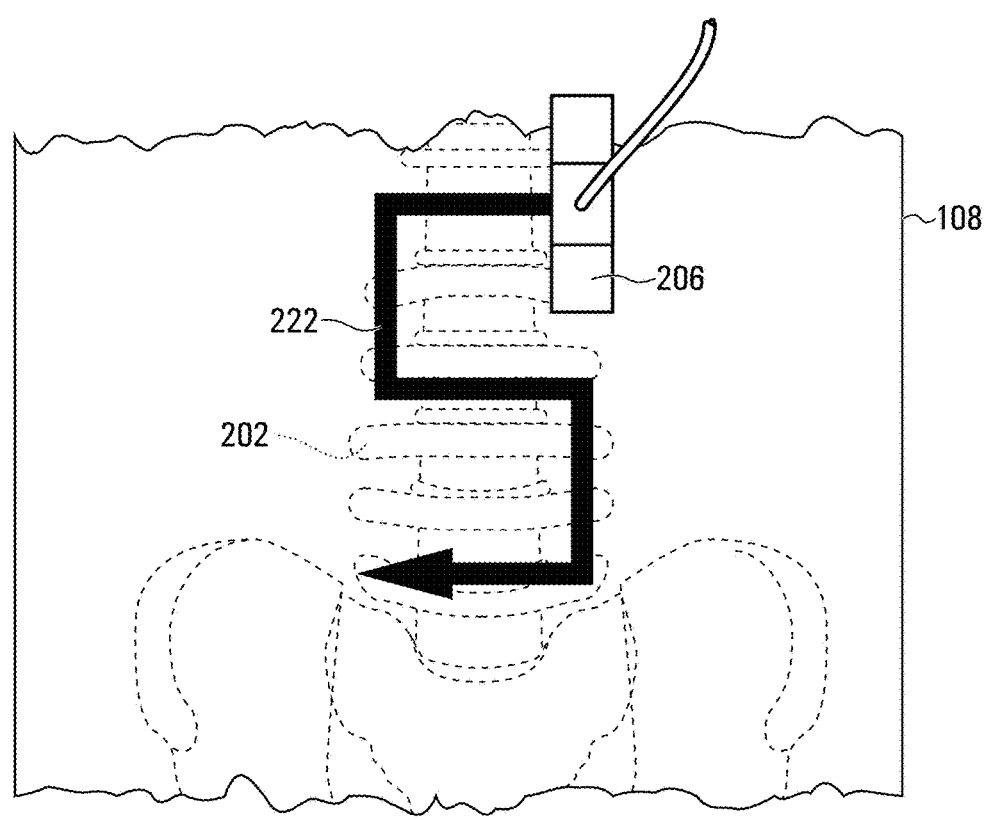
FIG. 10 is another illustration of the ultrasound probe of FIG. 6 over the lumbar vertebrae of the patient.

Moving the ultrasound probe 206 along a path relative to the patient 108 adds a third dimension to the data that the ultrasound probe 206 acquires, so two-dimensional ultrasonic datasets acquired using the ultrasound probe 206 may be combined into a three-dimensional ultrasonic dataset. To acquire an ultrasonic volumetric dataset of lumbar vertebrae 202 of the patient 108, the user may cause the ultrasound probe 206 to acquire a series of two-dimensional ultrasonic datasets. For example, FIG. 8 illustrates a "side sweep" path 218, FIG. 9 illustrates a "transverse midline" path 220, and FIG. 10 illustrates a "sagittal zigzag" path 222.

In some embodiments, more than one tracking reference may be placed on the patient 108, and in some other embodiments, the tracking reference 214 may be omitted. When the tracking reference 214 is omitted, the patient 108 may have to remain very still, or software in the ultrasound computer 216 may account for any movement of the patient 108 during scanning. In still other embodiments, the tracker 212 and the tracking reference 214 may be omitted, and the software in the ultrasound computer 216 may assemble a series of two-dimensional ultrasonic datasets into a three-dimensional ultrasonic dataset. In such embodiments, the patient's anatomy may replace the tracker because the stitching or mosaicing software may identify changes in position of the ultrasound probe without requiring a tracker.

Image Generation

Referring back to FIG. 2, the program memory 116 also includes image generation codes 224, which generally include blocks of code that direct the microprocessor 110 to generate an image for display on the display 106 as described below. The code in the image generation store 224 may include software executable directly by the microprocessor 110, or may include one or more scripts executable by MATLAB™ or another computer program.

Figure 11:
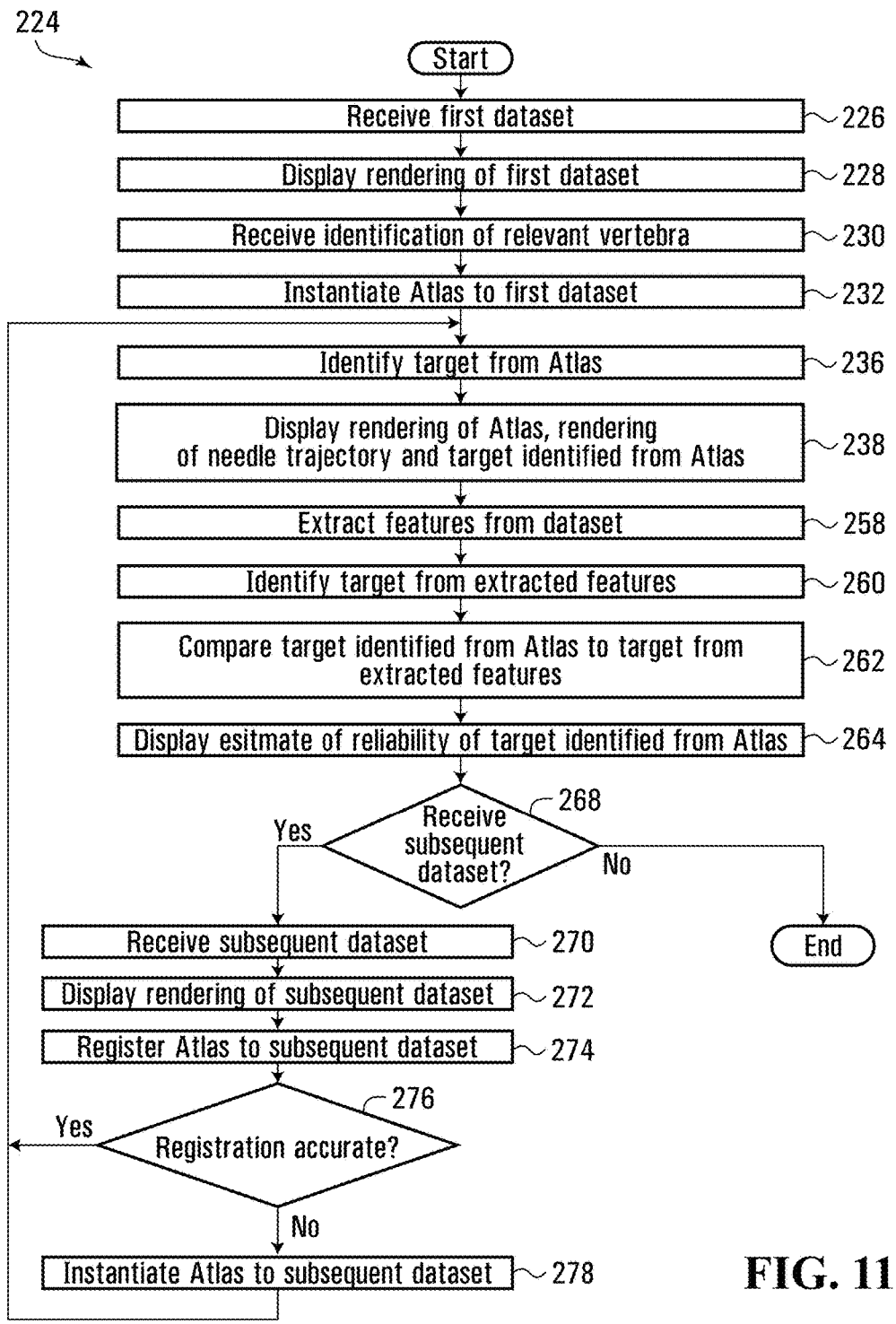
FIG. 11 is a schematic illustration of program code executed by the processor circuit of FIG. 2.

Referring to FIGS. 2 and 11, the image generation codes 224 are illustrated schematically and begin at block 226, which includes codes that direct the microprocessor 110 to receive a first ultrasonic volumetric dataset using the PLUS codes 198 and to store codes representing the first ultrasonic volumetric dataset in the ultrasonic volumetric dataset store 200. The image generation codes 224 then continue at block 228, which includes codes that direct the microprocessor 110 to cause the display 106 to display a rendering of the first ultrasonic volumetric dataset, and the image generation codes 224 that follow direct the microprocessor 110 to instantiate the three-dimensional atlas (represented by codes in the atlas store 122) according to the first ultrasonic volumetric dataset. The codes at block 228 may use a "3D Slicer" open-source software package (see http://www.slicer.org/for example) for visualization and image analysis. The rendering of the first ultrasonic volumetric dataset may be a cross-sectional view of the first ultrasonic volumetric dataset, a volume-rendered three-dimensional ray-traced image of the first ultrasonic volumetric dataset, or a "thick slice" generated from multiple planes in the first ultrasonic volumetric dataset. The "3D Slicer" interface may allow switches between various different such renderings.

Atlas Instantiation

As indicated above, "atlas" may refer to a statistical shape model or a statistical shape-and-pose model of anatomical features. Further, "instantiating" an atlas may refer to identification of weights for each mode of variation that approximate the atlas to anatomical features identified in an ultrasonic volumetric dataset. Further, "instantiating" may include a registration, or transformation, of the atlas into a common coordinate system as the ultrasonic volumetric dataset.

Atlases according to the embodiments described herein are "multi-body", "multi-bone", or "multi-vertebrae" atlases, which differ significantly from single-body atlases such as atlases of a single vertebra, of a single femur, or of a single pelvis for example, because such single-body atlases describe only one body or bone with no link to any other bodies or bones. In a multi-body atlas, modes of variation of at least two bodies are linked together, so that changing a weight of a mode of variation of the atlas may change the shape of more than one or all of the bodies in the atlas simultaneously.

Atlas instantiation in the embodiments described herein may involve enhancing bone surfaces in the ultrasonic volumetric dataset by computing a bone surface probability for each pixel by weighted summation of reflection amount (or pixel intensity) and shadowing effect. Pixels with large intensity and shadow underneath are assumed to be bone surface because bone surfaces are highly reflective of ultrasound waves. As described in Foroughi, P., Boctor, E., Swartz, M., Taylor, R., Fichtinger, G., "P6D-2 Ultrasound Bone Segmentation Using Dynamic Programming," *IEEE Ultrasonics Symposium* 13(4), 2523-2526 (2007), the image may be filtered with a Laplace of Gaussian ("LoG") of the ultrasound image and a shadow map, in which each pixel value corresponds to a weighted sum of the pixel values below the actual pixel, to calculate a reflectivity number and to extract high-intensity pixels. The result is added to the blurred image. Next, the blurred image is convoluted by a profile highlighting the shadow beneath a pixel. The shadow image is combined with the blurred image to generate a bone probability map V (X), which is the product of the shadow map and an image containing the reflectivity numbers. The bone probability map V (X) represents bone surface probabilities for each pixel in the ultrasonic volumetric dataset. Because the ultrasound probe in the embodiments described herein is positioned posterior-anterior, only the posterior aspect of each vertebra results in reflections that the ultrasound probe can detect. Similar to the approach of Winter, S., Brendel, B., Pechlivanis, I., Schmieder, K., and Igel, C., "Registration of CT and intraoperative 3-D ultrasound images of the spine using evolutionary and gradient-based methods," *IEEE Transactions on Evolutionary Computation* 12(3), 284-296 (2008), the points from the anterior surface are removed, leaving those points on the tip of spinous process, laminae, and facets.

For the atlas instantiation to converge to the correct target features, the model has to be initialized roughly at the correct position in the ultrasonic volumetric dataset. In some embodiments, a user is asked to locate the center of mass of a relevant vertebra (such as the L3 vertebra for example) in the rendering of the first ultrasonic volumetric dataset as displayed on the display 106 following the codes at block 228. Following block 228, the image generation codes 224 continue at block 230, which includes codes that direct the microprocessor 110 to receive the user location of the center of mass of the relevant vertebra, which may involve touching the display 106 if the display 106 is touch-sensitive, or which may involve using a pointing device such as a mouse (not shown). In other embodiments, however, block 230 may be omitted, and placing the ultrasound probe approximately midsaggital over vertebrae of interest may automatically define the initialization in inferior-superior and left-right directions. A posterior-anterior translation $t_{PA}$ may be calculated using the bone probability map V(X) according to $$t_{PA} = \frac{\sum_{f=l}^{F-r} \left[ \frac{\prod_{y=c}^{n_y} y \cdot \left[ \sum_{x=0}^{n_x} p_f(x, y) \right]}{\sum_{y=c}^{n_y} \sum_{x=0}^{n_x} p_f(x, y)} \right]}{F - r - l}, \qquad \text{(Eq. 5)}$$

where $p_f(x, y)$ is the pixel value of frame f in an ultrasonic volumetric dataset consisting of F frames, $n_x$ and $n_y$ are the number of pixels in the x and y directions respectively, c is a constant defined to disregard pixels close to the transducer array, and r and l are thresholds to disregard outer frames of the volumes consisting of mainly zero intensity pixels.

The image generation codes 224 then continue at block 232, which includes codes that direct the microprocessor 110 to instantiate the three-dimensional atlas (represented by codes in the atlas store 122) according to the first ultrasonic volumetric dataset. Instantiation of the atlas to the enhanced the ultrasonic volumetric dataset involves a GMM-based iterative technique. Boundary points of the atlas are defined as the centroids of the GMM, and the enhanced bone surface in the ultrasonic volumetric dataset is considered to be an observation generated by the GMM.

The instantiation is then an estimation of proper weights of the modes of variations, and of a rigid transformation applied to the entire enhanced bone surface, to maximize the probability of the GMM centroids generating the target. In one embodiment, the instantiation is parallelized at CPU level using the Intel™ Math Kernel Library. The codes at block 232 also direct the microprocessor 110 to store the values representing the weights, and the rigid transform, in an instance of atlas store 234 in the storage memory 114 shown in FIG. 2.

As indicated above, in an embodiment described above in which the atlas is a statistical shape-and-pose model, the atlas store 122 stores representations of eigenvalues $\lambda_{k,l}^p$ and $\lambda_{k,l}^s$, of eigenvectors $v_{k,l}^p$ and $v_{k,l}^s$, of a mean pose $\mu_l^p$, and of a mean shape $\mu_l^s$. In such an embodiment, $w_k^s$ is the weight applied to the kth principal geodesic for shape and $w_k^p$ is the weight applied to the kth principal geodesic for pose. The lth vertebra may be instantiated according to $$s_l = \Phi(w^s, w^p) = \Phi_l^p(\Phi_l^s(w^s); w^p), \quad (Eq. 6)$$

where $\Phi(\cdot, w_p)$ and $\Phi_l^s(\cdot)$ denote a similarity transformation and a shape, respectively, which are built by a combination of the principal geodesics of pose and shape with corresponding weights according to $$\Phi_l^p(\cdot; w^p) = \mu_l^p \prod_{k=1}^{K} \exp(w_k^p v_{k,l}^p) \quad (Eq. 7)$$

and $$\Phi_l^s(w^s) = \exp_{\mu_l^s} \sum_{k=1}^{K} (w_k^s v_{k,l}^s). \quad (Eq. 8)$$

The registration is performed using a GMM-based technique as discussed above from Rasoulian, A., Rohling, R., Abolmaesumi, P., "Group-wise registration of point sets for statistical shape models," *IEEE TMI* 31(11), 2025-2034 (2012). In such an iterative technique, soft-correspondences are established between surface of the model and the target that is represented by a point set. A correspondence function $P(x_n^l)$ is defined for $x_n^l$ (the nth point of N points on the lth vertebra of L vertebrae of the model) and $y_m$ (the mth point of M points on the target) and has a value between 0 and 1. The point set Y constitutes a partial surface of the vertebra and is extracted from the ultrasound images as explained above. Additionally, the bone surface probability extracted from the ultrasound images is already integrated into the correspondence function. The model is then instantiated and rigidly transformed to minimize the objective function $$Q = \sum_{l=1}^{L} \sum_{m,n=1}^{M,N} P(x_n^l \mid y_m) \|y_m - (R\Phi(x_n^l; w^s, w^p) + t)\|^2 + \quad (Eq. 9)$$

$$\gamma^s \Gamma^s w^s + \gamma^p \Gamma^p w^p$$

where the two last terms are the regularization over the weights of the principal geodesics, and $\Gamma^s$ and $\Gamma^p$ are diagonal matrices with elements $1/\lambda^s$ and $1/\lambda^p$, the corresponding eigenvalues of the shape and the pose principal geodesics, respectively. The matrices R and t are the rotation and translation of the rigid transformation, respectively. The optimization may be performed using a Quasi-Newton method. As a result, the objective function of Eq. 9 is minimized with respect to the points of the model that are visible in ultrasound volumes, which may include laminae, spinous processes, articular processes, or transverse processes, or a combination of two or more thereof, of one side only or of both sides.

In general, the atlas may include a large number of modes of variation. Instantiation using a relatively large number of modes of variation may produce more accurate results, but instantiation using a relatively small number of modes of variation may be faster. In some embodiments, about 10 to about 12 of the most important modes of variation (that is, the modes of variation associated with the largest eigenvalues) may appropriately balance accuracy and speed.

Target Identification from the Atlas

After block 232, the image generation codes 224 continue at block 236, which includes codes that direct the microprocessor 110 to identify an injection target from the instantiation of the atlas. Different applications may involve different injection targets. For example, the injection target for an epidural injection is an epidural space in the outermost part of the spinal canal of a patient (formed by the two surrounding vertebrae), and the injection target for a facet joint injection is a facet joint between adjacent vertebrae of a patient. Identifying such an injection target from an instantiation of the atlas may involve identifying anatomical features of two adjacent vertebrae as identified in the instantiation of the atlas and estimating the injection target relative to the identified anatomical features.

For example, the epidural space is between the dura mater and the ligamentum flavum, and for an epidural needle insertion, the codes at block 236 may direct the microprocessor 110 to identify a likely location of the patient's dura mater according to anatomical features of two adjacent vertebrae as identified in the instantiation of the atlas, to identify a likely location of the ligamentum flavum according to anatomical features of two adjacent vertebrae as identified in the instantiation of the atlas, to identify a possible needle trajectory between spinous processes and other anatomical features of two adjacent vertebrae as identified in the instantiation of the atlas, and to identify a location for the epidural injection along the identified needle trajectory and between the identified locations of the dura mater and of the ligamentum flavum.

As another example, facet joints are between articular processes of adjacent vertebrae, and for a facet joint injection, the codes at block 236 may direct the microprocessor 110 to identify a likely location of an articular process of one vertebra, to identify a likely location of an articular process of an adjacent vertebra, and to identify a location for the facet joint injection between the identified articular processes.

Augmented Image Display

After block 236, the image generation codes 224 continue at block 238, which includes codes that direct the microprocessor 110 to augment the rendering of the ultrasonic volumetric dataset as displayed on the display 106 following the codes at block 228.

Figure 12:
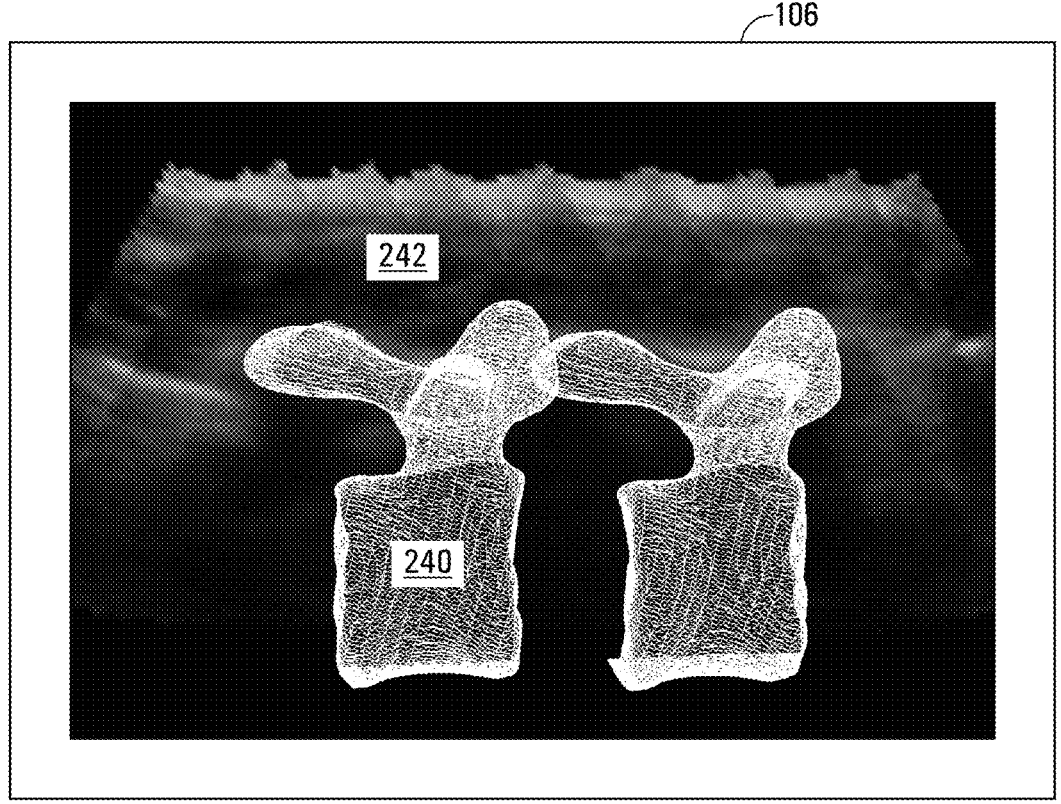
FIG. 12 is an example of an augmented image on a display of the image generation system of FIG. 1.
Figure 13:
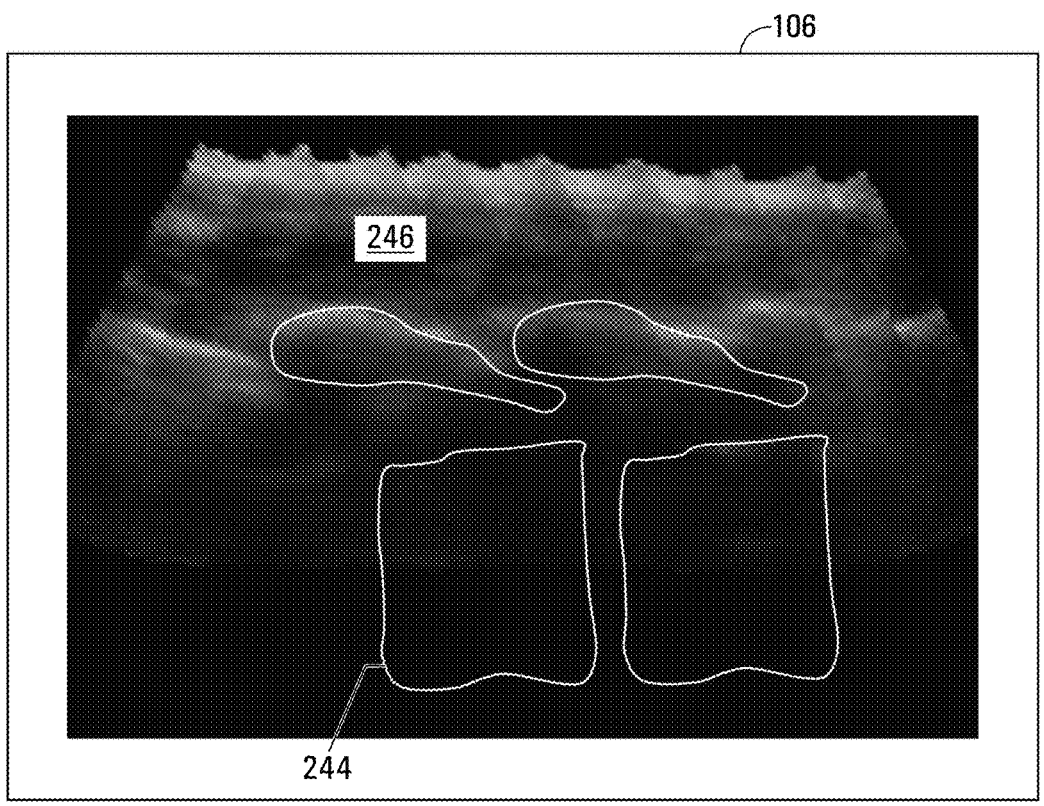
FIG. 13 is another example of an augmented image on a display of the image generation system of FIG. 1.
Figure 14:
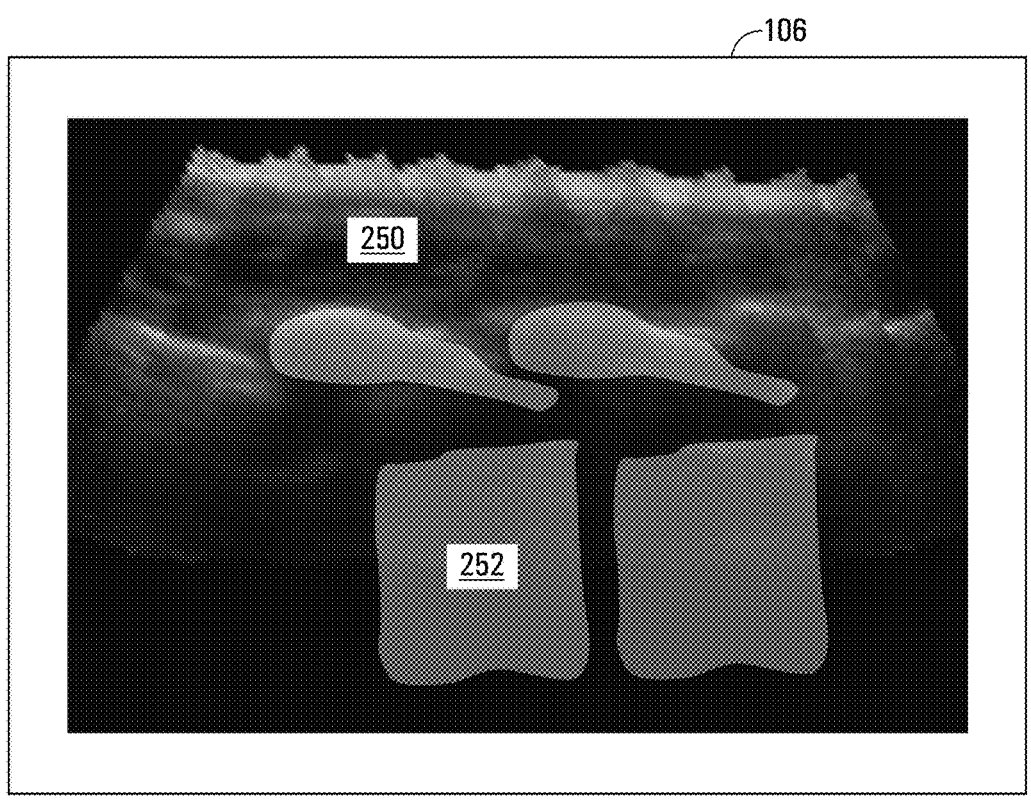
FIG. 14 is another example of an augmented image on a display of the image generation system of FIG. 1.
Figure 15:
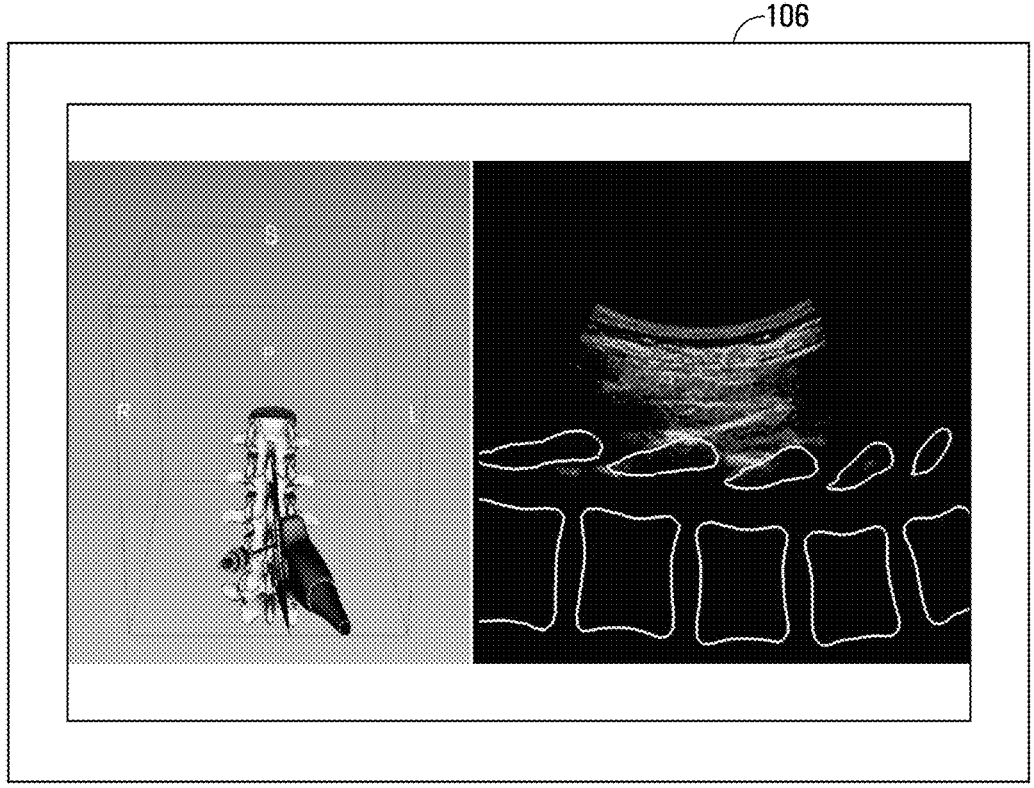
FIG. 15 is another example of an augmented image on a display of the image generation system of FIG. 1.

Specifically, the codes at block 238 direct the microprocessor 110 to superimpose, on the display 106 and over the rendering of the ultrasonic volumetric dataset, a rendering of the instantiated atlas. For example, FIG. 12 illustrates a three-dimensional wire-mesh rendering 240 of the instantiated atlas over a rendering 242 of the ultrasonic volumetric dataset on the display 106. As another example, FIG. 13 illustrates an outline rendering 244 of the instantiated atlas over a rendering 246 of the ultrasonic volumetric dataset on the display 106. As another example, FIG. 14 illustrates a cross-sectional rendering 252 of the instantiated atlas over a rendering 250 of the ultrasonic volumetric dataset on the display 106. As another example, FIG. 15 illustrates a split view including a three-dimensional rendering of the instantiated atlas on one side of the display 106, and an outline rendering over a rendering of the ultrasonic volumetric dataset on the other side of the display 106. In other embodiment, the rendering of the instantiated atlas may be a shaded surface, or a semi-transparent shaded surface, of the atlas. In general, renderings of the instantiated atlas may illustrate portions of, or all of, the instantiated atlas.

Figure 16:
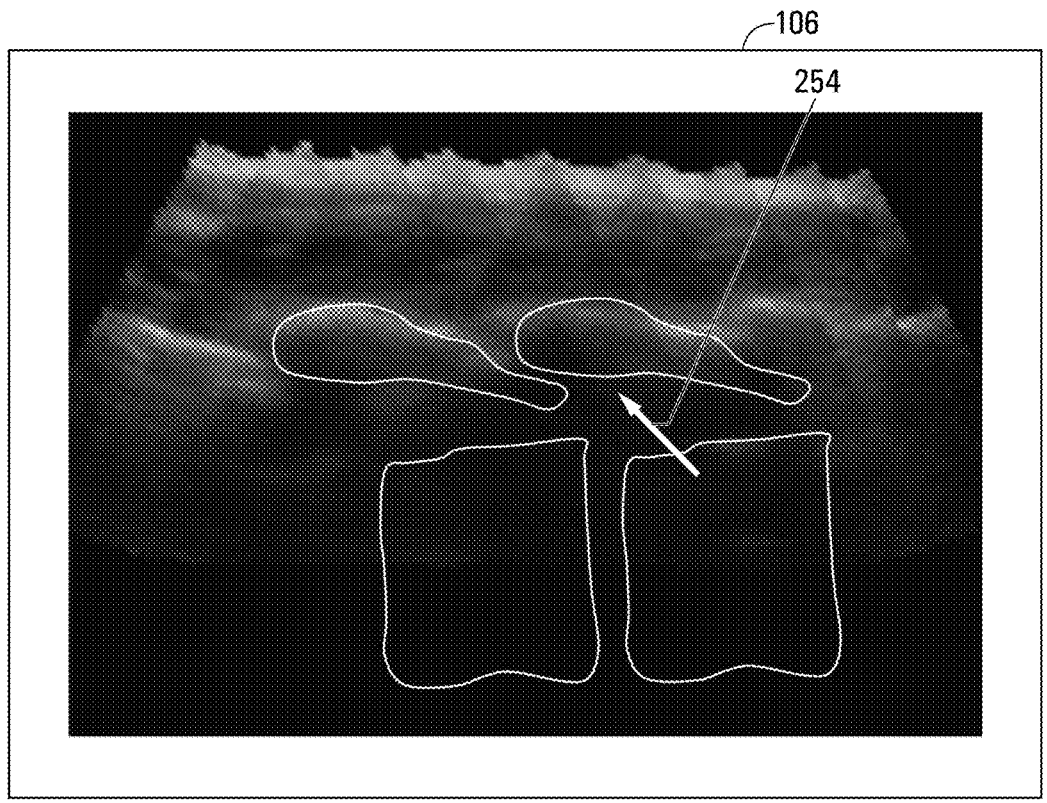
FIG. 16 is another example of an augmented image on a display of the image generation system of FIG. 1.
Figure 17:
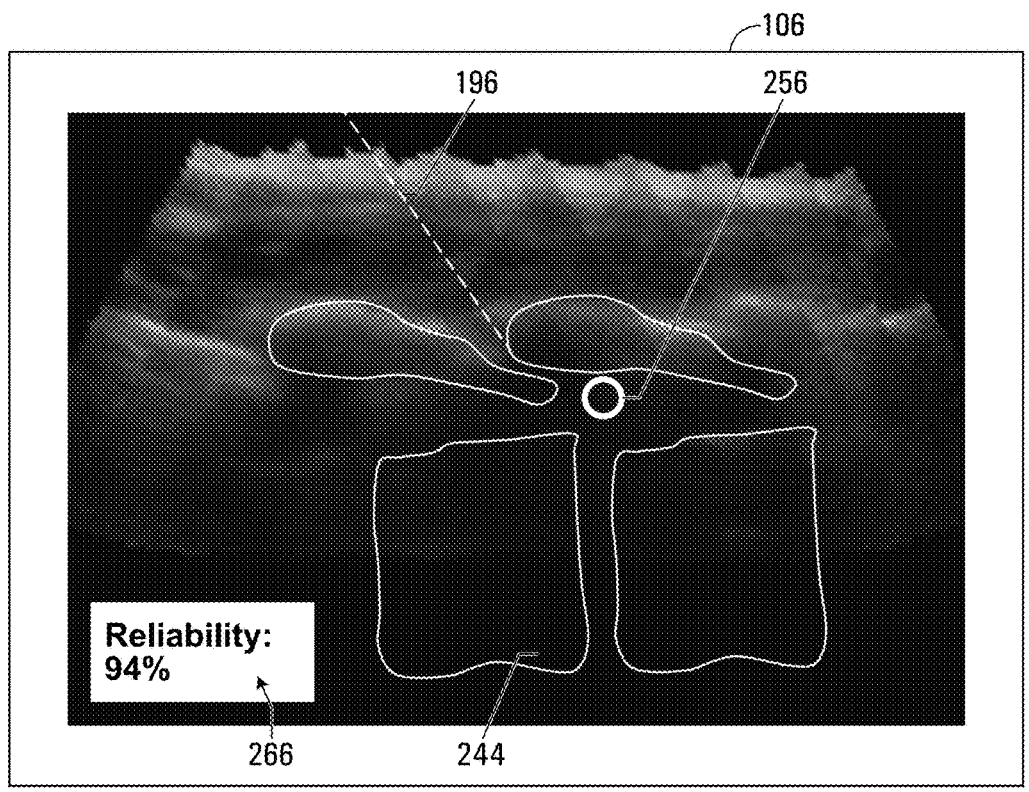
FIG. 17 is another example of an augmented image on a display of the image generation system of FIG. 1.

As indicated above, the codes at block 236 direct the microprocessor 110 to identify an injection target from the instantiation of the atlas. The codes at block 238 may also direct the microprocessor 110 to superimpose, on the display 106 and over the rendering of the ultrasonic volumetric dataset, an icon pointing to the injection target. For example, FIG. 16 illustrates an arrow 254 pointing to an injection target, and FIG. 17 illustrates a circle 256 indicating the injection target. More generally, the codes at block 238 may direct the microprocessor 110 to highlight the target that was identified from the instantiation of the atlas on the display 106.

As indicated above, in some embodiments, an ultrasound probe (such as the ultrasound probe 104) may include a needle guide to receive a portion of an injection needle and guide the injection needle along a needle trajectory. In embodiments in which an ultrasound probe includes a needle guide defining a needle trajectory, the codes at block 238 may direct the microprocessor 110 to superimpose, on the display 106 and over the rendering of the ultrasonic volumetric dataset, a rendering of the needle trajectory. For example, FIG. 17 also illustrates the needle trajectory 196 calculated according to the position of the ultrasound probe 104.

In embodiments including an ultrasound probe (such as the ultrasound probe 206) that does not include a needle guide, an electromagnetic tracker (such as the electromagnetic tracker 212) may track a position of an injection needle, and in such embodiments, the position or trajectory, or both, of the injection needle according to the electromagnetic tracker may be displayed on the display 106.

In still other embodiments, an ultrasound probe (such as the ultrasound probe 104) may continuously produce ultrasonic volumetric datasets (which are identified as subsequent ultrasonic volumetric datasets at block 268 as described below), and an injection needle may appear in such continuously produced ultrasonic volumetric datasets. Therefore, displaying such continuously produced ultrasonic volumetric datasets on the display 106 may cause the display to illustrate a measured position of the injection needle.

Feature Extraction

Independently from instantiation of the atlas, features may be extracted from an ultrasonic volumetric dataset such as the ultrasonic volumetric datasets discussed above. After block 238, the image generation codes 224 continue at block 258, which includes codes that direct the microprocessor 110 to extract features from the ultrasonic volumetric dataset by recursively partitioning image data from ultrasonic planes of the ultrasonic volumetric dataset.

Recursively partitioning image data from ultrasonic planes involves decomposing the image data at a scale j into four patches, and to repeat the recursive procedure to a depth δ. The optimum decomposition scale δ may be chosen based on measuring the classification accuracy for various values of δ. In one study, the best correct classification rate was achieved with three levels of decomposition (δ=3). If $P_j$ is a list of all decomposed images at a scale j, then for all j≤δ and for all S∈$P_j$, $$C^{Pj} = \langle H^j \times S_k \times H^{jT} \rangle k=1, \ldots, |P_j| \qquad \text{(Eq. 10)}$$

is a list of Recursive Partitioning Hadamard Coefficients ("RPHC") of image patches where $H^j$ is a local directional Hadamard matrix at a the scale j and $H^{jT}$ is the transpose of $H^j$. A local directional Hadamard matrix for a size m of the transform may be defined recursively as $$H_m = \frac{1}{\sqrt{2}} \begin{pmatrix} H_{m/2} & H_{m/2} \\ H_{m/2} & -H_{m/2} \end{pmatrix} \qquad \text{(Eq. 11)}$$

where m is a positive-integer power of 2 and $H_1=1$.

A two-dimensional Hadamard transform provides sequency representation of an image along vertical and horizontal directions, and may thus in detect different structures within the image. More particularly, patterns of different spinal structures may be identified by finding a region-orientation correlation of signatures in the sequency domain. The codes at block 258 direct the microprocessor 110 to filter Hadamard coefficients according to crisp wedge filters $F_{vt}$, $F_{hr}$, and $F_{dg}$ in the Hadamard domain, where $F_{vt}$ masks the Hadamard coefficients except those that correspond to vertical patterns, $F_{hr}$ masks the Hadamard coefficients except those that correspond to horizontal patterns, and $F_{dg}$ masks the Hadamard coefficients except those that correspond to diagonal patterns. In one embodiment, $F_{vt}$ is defined as $$F_{vt}(u, v, \alpha) = \frac{1}{2} + \frac{1}{2} \frac{\left| v - \frac{ua}{50} \right|}{v - \frac{ua}{50}} \qquad \text{(Eq. 12)}$$

where u and v are sequency domain indices and α is a parameter that defines a percentage of covered area (α<50). $F_{hr}$ and $F_{vt}$ are symmetric, so $$F_{hr} = F_{vt}^T \qquad \text{(Eq. 13)}$$

and $$F_{dg} = 1 - F_{vt} - F_{hr} \qquad \text{(Eq. 14)}$$

to cover the remaining area of the transformed matrix.

The parameter α also tunes the precision of the filters. Small values of α correspond to a narrower range of angles, whereas a large α translates into wider range of angles for such structures. Therefore, choosing the right α depends on the application. In one study, to find the optimum value for the wedge filter coverage area parameter α, vertical, horizontal, and diagonal feature vectors were extracted separately from samples of different classes (such as lamina, facet, and non-target classes). The optimum value for the wedge filter coverage area parameter α causes the filters to yield distinctive vertical, horizontal, and diagonal features from laminae, facet joints, and non-target planes of an ultrasonic volumetric datasets. Therefore, the optimal wedge filters would give orthogonal or nearly orthogonal intraclass feature vectors, and the intraclass distance between feature vectors should be maximized, and intraclass dot products of vertical, horizontal, and diagonal features, or similarity vectors $v_s$, were calculated for 5≤α≤45 from an entire dataset. To ensure maximum orthogonality, the three feature were minimized simultaneously, and the $l_2$ norm of the similarity vectors in three-dimensional feature space was minimized. In one study, the classifier reached its maximum performance with α=15.

The codes at block 258 direct the microprocessor 110 to extract features from an ultrasonic volumetric dataset by training a statistical learning algorithm, such as a two-layer artificial neural network for example, for pattern classification. In one study, a two-layer artificial neural network reached its maximum performance with 35 neurons in the hidden layer. In one embodiment, a hyperbolic tangent sigmoid function is used in the hidden layers, softmax activation functions are used in the output layer, and the network weights are updated using a scaled conjugate gradient algorithm. Although feature extraction has been described above together with instantiation of an atlas, feature extraction as described herein may, in other embodiments, have more general applications that are not necessarily related to an atlas or to identification of targets for injections.

Estimating Reliability

After block 258, the image generation codes 224 continue at block 260, which includes codes that direct the microprocessor 110 to identify an injection target from the features extracted at block 258. As with the codes at block 236, the codes at block 260 may direct the processor 110 to identify an epidural space in a spinal canal of a patient, or may identify a facet joint between adjacent vertebrae of a patient.

After block 260, the image generation codes 224 continue at block 262, which includes codes that direct the microprocessor 110 to compare the injection target identified from the instantiation of the atlas at block 236 to the injection target identified from the extracted features at block 260. Where the injection target identified from the instantiation of the atlas at block 236 is close to the injection target identified from the extracted features at block 260, the identification of the injection target from the instantiation of the atlas at block 236 may be considered reliable. Therefore, the codes at block 262 direct the processor 110 to calculate a reliability estimate from the comparison of the injection target identified from the instantiation of the atlas at block 236 to the injection target identified from the extracted features at block 260. For example, the reliability estimate may be a distance between the injection target identified from the instantiation of the atlas at block 236 to the injection target identified from the extracted features at block 260. As another example, the reliability estimate may be a reliability score or percentage calculated as a function of the distance between the injection target identified from the instantiation of the atlas at block 236 to the injection target identified from the extracted features at block 260.

After block 262, the image generation codes 224 continue at block 264, which includes codes that direct the microprocessor 110 to cause the display 106 to display the reliability estimate calculated at block 262. As one example, FIG. 17 illustrates a reliability estimate 266 on the display 106.

Subsequent Ultrasonic Volumetric Datasets

Using current technology, a new ultrasonic volumetric dataset can be acquired in less than one second. Therefore, the ultrasound probe may continuously acquire ultrasonic volumetric datasets, and with each ultrasonic volumetric dataset, the instantiation of the atlas may be updated to reflect the current position of the ultrasound probe as the ultrasound probe moves relative to the patient. Such updates in less than one second may allow "real-time" use of a stream of ultrasonic volumetric datasets and "real-time" updating of the augmented image on the display 106.

After block 264, the image generation codes 224 continue at block 268, which includes codes that direct the microprocessor 110 to determine whether an ultrasonic volumetric dataset, subsequent to the ultrasonic volumetric dataset currently stored in the ultrasonic volumetric dataset store 200, will be received. The user may indicate that no subsequent ultrasonic volumetric dataset will be received, in which case the image generation codes 224 terminate. However, if a subsequent ultrasonic volumetric is received, then the image generation codes 224 continue at block 270, which includes codes that direct the microprocessor 110 to receive the subsequent ultrasonic volumetric dataset using the PLUS codes 198 and to store codes representing the subsequent ultrasonic volumetric dataset in the ultrasonic volumetric dataset store 200 as described above. The image generation codes 224 then continue at block 272, which includes codes that direct the microprocessor 110 to cause the display 106 to display a rendering of the subsequent ultrasonic volumetric dataset. Again, the codes at block 272 may use the "3D Slicer" open-source software package for visualization and image analysis.

As indicated above, the codes at block 232 direct the microprocessor 110 to estimate proper weights of the modes of variations, and of a rigid transformation applied to the entire enhanced bone surface, and to store the values representing the weights, and the rigid transform, in an instance of atlas store 234 in the storage memory 114 shown in FIG. 2. In many cases, the subsequent ultrasonic volumetric dataset represents measurements from an ultrasound probe in a different position or different orientation from the previous ultrasonic volumetric dataset. Therefore, after block 272, the image generation codes 224 continue at block 274, which includes codes that direct the microprocessor 110 to attempt to register the subsequent ultrasonic volumetric dataset by updating only the rigid transformation. The codes at block 274 direct the microprocessor 110 to generate a bone probability map from the subsequent ultrasonic volumetric dataset as described above. Then, the rigid transform is updated according to $$Q = \sum_{l=1}^{L} \sum_{m,n=1}^{M,N} P(x_n^l \mid y_m) \|y_m - (R\Phi(x_n^l; \tilde{w}^s, \tilde{w}^p) + t)\|^2 \quad \text{(Eq. 15)}$$

where $\tilde{w}^s$ and $\tilde{w}^p$ are the best-fitting shape and pose respectively of the previous instantiation, and the remaining terms are discussed above regarding Eq. 9. Alternatively, the rigid transform may be updated by registering the subsequent ultrasonic volumetric dataset to the previous ultrasonic volumetric dataset by pair-wise image-based registration with a maximum correlation between the two ultrasonic volumetric datasets. Again, the Intel™ Math Kernel Library may reduce computation time for updating the rigid transform.

By registering the subsequent ultrasonic volumetric dataset to the previously instantiated atlas or to the previous ultrasonic volumetric dataset, the patient's anatomy is used to track movement of the ultrasound probe, which may avoid the need for an electromagnetic tracker. However, in other embodiments, a tracker and a tracking reference (such as the tracker 212 and the tracking reference 214) may facilitate registration of the subsequent ultrasonic volumetric dataset by measuring movement of the ultrasound probe relative to the patient.

After block 274, the image generation codes 224 continue at block 276, which includes codes that direct the microprocessor 110 to determine whether the instantiation remains sufficiently accurate following only the update to the rigid transformation at block 274. For example, in one embodiment, the codes at block 276 direct the microprocessor 110 to calculate a mean surface error of the instantiation following the update to only the rigid transformation, and determining whether the mean surface error exceeds a threshold.

If at block 276 the instantiation remains sufficiently accurate, for example because the mean surface error does not exceed the threshold, then the image generation codes 224 continue at block 236 as discussed above. However, if at block 276 the instantiation does not remain sufficiently accurate, for example because the mean surface error exceeds the threshold, then the image generation codes 224 continue at block 278, which includes codes that direct the microprocessor 110 to repeat the instantiation as described above for block 232, and then the image generation codes 224 continue at block 236 as discussed above.

When the image generation codes 224 return block 236 after block 276 or block 278, the process of identifying a target at block 236, displaying at block 238, extracting features at block 258, identifying a target at block 260, comparing the identified targets at block 262, and displaying the estimate at block 264 are as described above, except those processes are based on the subsequent ultrasonic volumetric dataset received at block 270 and on the updated atlas from block 274 (and possibly from block 278) as described above. The image generation codes 224 thus continuously update the augmented display until at block 268 the user indicates that no subsequent ultrasonic volumetric dataset will be received.

Applications

In general, embodiments such as those described above may augment an image from ultrasound data with an image of an atlas of at least two vertebrae, which may be a more accurate atlas than an atlas of a single vertebra, or than a plurality of atlases each of a single vertebra, because an atlas of at least two vertebrae, as in the embodiments described above, may account for similar variations in different vertebrae.

Further, embodiments such as those described above may estimate positions of targets, either from an atlas or from extracted features from an ultrasonic volumetric dataset, or from both, according to anatomical features of two adjacent vertebrae, which may assist in positioning a needle trajectory such as the needle trajectory 196 shown in FIGS. 3, 4, and 17.

Because the augmented image of the embodiments described above may update to reflect a new ultrasonic volumetric dataset in less than one second, an ultrasound probe (such as the ultrasound probe 104) may conveniently be positioned and oriented relative to a patient until the needle trajectory 196 intersects an injection target such as an epidural space or a facet joint. Alternatively, the position or trajectory (or both) of an injection needle may be superimposed on an augmented image, so that the injection needle may be moved independently of an ultrasound probe until the trajectory of injection needle intersects the injection target. Accordingly, embodiments such as those described above may facilitate positioning a needle close to an injection target with more accurate information than some other augmented images may provide.

Although specific embodiments have been described and illustrated, such embodiments should be considered illustrative only and not as limiting the invention as construed according to the accompanying claims.

The invention claimed is:

1. A computer-implemented method of producing an augmented image of a spine of a patient, the method comprising:
  receiving a first ultrasonic volumetric dataset representing a three-dimensional depiction of anatomical features of the spine in a first volume;
  instantiating a three-dimensional atlas of at least two vertebrae according to the first ultrasonic volumetric dataset, wherein the atlas links together modes of variation of at least a mean shape of the at least two vertebrae; and
  causing a display to display a rendering of the first ultrasonic volumetric dataset together with a rendering of the atlas.

2. The method of claim 1 further comprising:
  receiving a second ultrasonic volumetric dataset representing a three-dimensional depiction of anatomical features of the spine in a second volume different from the first volume;
  registering the three-dimensional atlas according to the second ultrasonic volumetric dataset, wherein registering the atlas comprises updating a rigid transform of the atlas according to the second ultrasonic volumetric dataset; and
  causing the display to display a rendering of the second ultrasonic volumetric dataset and a rendering of the registered atlas.

3. The method of claim 1 wherein instantiating the three-dimensional atlas according to the first ultrasonic volumetric dataset comprises:
  identifying a rigid-body transformation that aligns the mean shape to the first ultrasonic volumetric dataset; and
  identifying weights for respective modes of variation of the mean shape.

4. The method of claim 3 wherein instantiating the three-dimensional atlas according to the first ultrasonic volumetric dataset further comprises:
  identifying weights for respective modes of variation of a mean pose representing relative positions in the spine of the at least two vertebrae of the three-dimensional atlas.

5. The method of claim 1 wherein receiving the first ultrasonic volumetric dataset comprises receiving the first ultrasonic volumetric dataset from an ultrasonic probe defining a needle guide.

6. The method of claim 5 further comprising causing the display to display a rendering of an anticipated trajectory of a needle in the needle guide.

7. The method of claim 1 further comprising identifying a target defined by two of the at least two vertebrae of the atlas.

8. The method of claim 7 further comprising:
  extracting features from the first ultrasonic volumetric dataset;
  identifying a target defined by two of the at least two vertebrae of the extracted features from the first ultrasonic volumetric dataset;
  generating a comparison of the target defined by two of the at least two vertebrae of the atlas to the target defined by two of the at least two vertebrae of the extracted features from the first ultrasonic volumetric dataset; and causing the display to display an estimation of reliability of the target defined by two of the at least two vertebrae of the atlas.

9. The method of claim 8 wherein extracting the features from the first ultrasonic volumetric dataset comprises:
  recognizing the features in at least some planes in the first ultrasonic volumetric dataset; and
  classifying patterns in the features in the at least some planes in the first ultrasonic volumetric dataset.

10. The method of claim 9 wherein recognizing the features in the at least some planes in the first ultrasonic volumetric dataset comprises:
  transforming portions the at least some planes in the first ultrasonic volumetric dataset into a sequency domain; and
  filtering the sequency domain.

11. The method of claim 9 wherein classifying the patterns in the features in the at least some planes in the first ultrasonic volumetric dataset comprises receiving outputs from a statistical learning algorithm trained to classify patterns in human spines.

12. An apparatus for producing an augmented image of a spine of a patient, the apparatus comprising:
  a display; and
  at least one processor circuit in communication with the display and configured to:
    receive a first ultrasonic volumetric dataset representing a three-dimensional depiction of anatomical features of the spine in a first volume;
    instantiate a three-dimensional atlas of at least two vertebrae according to the first ultrasonic volumetric dataset, wherein the atlas links together modes of variation of at least a mean shape of the at least two vertebrae; and
    cause the display to display a rendering of the first ultrasonic volumetric dataset together with a rendering of the atlas.

13. The apparatus of claim 12 wherein the at least one processor circuit is further configured to:
  receive a second ultrasonic volumetric dataset representing a three-dimensional depiction of anatomical features of the spine in a second volume different from the first volume;
  register the three-dimensional atlas according to the second ultrasonic volumetric dataset, wherein the at least one processor circuit is configured to register the atlas by updating a rigid transform of the atlas according to the second ultrasonic volumetric dataset; and
  cause the display to display a rendering of the second ultrasonic volumetric dataset and a rendering of the registered atlas.

14. The apparatus of claim 12 wherein the at least one processor circuit is configured to instantiate the three-dimensional atlas according to the first ultrasonic volumetric dataset by:
  identifying a rigid-body transformation that aligns the mean shape to the first ultrasonic volumetric dataset; and
  identifying weights for respective modes of variation of the mean shape.

15. The apparatus of claim 14 wherein the at least one processor circuit is further configured to instantiate the three-dimensional atlas according to the first ultrasonic volumetric dataset by:
  identifying weights for respective modes of variation of a mean pose representing relative positions in the spine of the at least two vertebrae of the three-dimensional atlas.

16. The apparatus of claim 12 further comprising an ultrasonic probe in communication with the at least one processor circuit, wherein the ultrasonic probe defines a needle guide.

17. The apparatus of claim 16 wherein the at least one processor circuit is further configured to cause the display to display a rendering of an anticipated trajectory of a needle in the needle guide.

18. The apparatus of claim 12 wherein the at least one processor circuit is further configured to identify a target defined by two of the at least two vertebrae of the atlas.

19. The apparatus of claim 18 wherein the at least one processor circuit is further configured to:
  extract features from the first ultrasonic volumetric dataset;
  identify a target defined by two of the at least two vertebrae of the extracted features from the first ultrasonic volumetric dataset;
  generate a comparison of the target defined by two of the at least two vertebrae of the atlas to the target defined by two of the at least two vertebrae of the extracted features from the first ultrasonic volumetric dataset; and
  cause the display to display an estimation of reliability of the target defined by two of the at least two vertebrae of the atlas.

20. The apparatus of claim 19 wherein the at least one processor circuit is configured to extract the features from the first ultrasonic volumetric dataset by:
  recognizing the features in at least some planes in the first ultrasonic volumetric dataset; and
  classifying patterns in the features in the at least some planes in the first ultrasonic volumetric dataset.

21. The apparatus of claim 20 wherein the at least one processor circuit is configured to recognize the features in the at least some planes in the first ultrasonic volumetric dataset by:
  transforming portions the at least some planes in the first ultrasonic volumetric dataset into a sequency domain; and
  filtering the sequency domain.

22. The apparatus of claim 20 wherein the at least one processor circuit is configured to classify the patterns in the features in the at least some planes in the first ultrasonic volumetric dataset by receiving outputs from a statistical learning algorithm trained to classify patterns in human spines.

23. The method of claim 1 wherein causing the display to display the rendering of the atlas comprises causing the display to display a rendering of at least a portion of each of the at least two vertebrae simultaneously.

24. The apparatus of claim 12 wherein the at least one processor circuit is configured to cause the display to display the rendering of the atlas by causing the display to display a rendering of at least a portion of each of the at least two vertebrae simultaneously.

* * * * *